(12) United States Patent
Abdulhalim et al.

(10) Patent No.: US 9,476,698 B2
(45) Date of Patent: *Oct. 25, 2016

(54) PERIODIC PATTERNS AND TECHNIQUE TO CONTROL MISALIGNMENT BETWEEN TWO LAYERS

(71) Applicant: KLA-Tencor Corporation, Milpitas, CA (US)

(72) Inventors: Ibrahim Abdulhalim, Kfar Manda (IL); Mike Adel, Zichron Ya'akov (IL); Michael Friedmann, Nesher (IL); Michael Faeyrman, Kiryat Motzkin (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/961,629

(22) Filed: Dec. 7, 2015

(65) Prior Publication Data

US 2016/0084639 A1 Mar. 24, 2016

Related U.S. Application Data

(63) Continuation of application No. 14/789,796, filed on Jul. 1, 2015, now Pat. No. 9,234,745, which is a continuation of application No. 14/035,766, filed on Sep. 24, 2013, now Pat. No. 9,103,662, which is a (Continued)

(51) Int. Cl.
*G01B 11/00* (2006.01)
*G01B 11/14* (2006.01)
(Continued)

(52) U.S. Cl.
CPC .............. *G01B 11/14* (2013.01); *G01B 11/26* (2013.01); *G01N 21/9501* (2013.01);
(Continued)

(58) Field of Classification Search
CPC ....... G01B 11/27; G01B 11/272; G03F 9/70; G03F 7/70358; H01L 21/681
USPC ......................................................... 356/399
See application file for complete search history.

(56) References Cited

U.S. PATENT DOCUMENTS 3,520,584 A * 7/1970 Kogelnik ................ G03H 1/00
359/11
3,546,374 A * 12/1970 Graser, Jr. .............. G02B 27/46
348/336

(Continued)

FOREIGN PATENT DOCUMENTS

DE 19925831 A1 12/2000
EP 0965889 A2 12/1999

(Continued)

OTHER PUBLICATIONS

Arkhipov et al., "Kinetics of the diffraction efficiency of light-induced dynamic gratings in layers of disordered semiconductors," Quantum Electronics, vol. 23, Issue 11, 1993 pp. 986-988.

(Continued)

*Primary Examiner* — Tarifur Chowdhury
*Assistant Examiner* — Md M Rahman
(74) *Attorney, Agent, or Firm* — Kwan & Olynick LLP

(57) ABSTRACT

A method and system to measure misalignment error between two overlying or interlaced periodic structures are proposed. The overlying or interlaced periodic structures are illuminated by incident radiation, and the diffracted radiation of the incident radiation by the overlying or interlaced periodic structures are detected to provide an output signal. The misalignment between the overlying or interlaced periodic structures may then be determined from the output signal.

13 Claims, 22 Drawing Sheets

Related U.S. Application Data continuation of application No. 12/628,092, filed on Nov. 30, 2009, now Pat. No. 8,570,515, which is a continuation of application No. 12/428,401, filed on Apr. 22, 2009, now Pat. No. 8,525,994, which is a continuation of application No. 11/495,001, filed on Jul. 27, 2006, now abandoned, which is a continuation of application No. 11/355,613, filed on Feb. 15, 2006, now abandoned, which is a continuation of application No. 11/062,255, filed on Feb. 18, 2005, now abandoned, which is a continuation of application No. 10/682,544, filed on Oct. 8, 2003, now abandoned, which is a continuation of application No. 09/833,084, filed on Apr. 10, 2001, now abandoned.

(51) Int. Cl.
  *G03F 7/20* (2006.01)
  *H01L 21/66* (2006.01)
  *H01L 23/544* (2006.01)
  *G01B 11/26* (2006.01)
  *G01N 21/95* (2006.01)

(52) U.S. Cl.
  CPC .......... *G03F 7/70633* (2013.01); *H01L 22/12* (2013.01); *H01L 23/544* (2013.01); *H01L 2223/54453* (2013.01); *H01L 2924/0002* (2013.01)

(56) References Cited

U.S. PATENT DOCUMENTS

| | | | |
|---|---|---|---|
| 3,548,643 A * | 12/1970 | Leith | G03H 1/00 356/457 |
| 3,549,238 A * | 12/1970 | Graser, Jr. | G03C 7/00 353/20 |
| 4,103,998 A | 8/1978 | Nakazawa et al. | |
| 4,124,458 A | 11/1978 | Moeglich | |
| 4,167,337 A | 9/1979 | Jaerisch et al. | |
| 4,200,395 A | 4/1980 | Smith et al. | |
| 4,332,473 A | 6/1982 | Ono | |
| 4,340,305 A | 7/1982 | Smith et al. | |
| 4,408,884 A | 10/1983 | Kleinknecht et al. | |
| 4,631,416 A | 12/1986 | Trutna, Jr. | |
| 4,703,434 A | 10/1987 | Brunner | |
| 4,750,836 A | 6/1988 | Stein | |
| 4,757,207 A | 7/1988 | Chappelow et al. | |
| 4,818,110 A | 4/1989 | Davidson | |
| 4,820,055 A | 4/1989 | Muller | |
| 4,828,392 A | 5/1989 | Nomura et al. | |
| 4,848,911 A | 7/1989 | Uchida et al. | |
| 4,889,998 A | 12/1989 | Hayano et al. | |
| 4,929,083 A | 5/1990 | Brunner | |
| 4,999,014 A | 3/1991 | Gold et al. | |
| 5,020,910 A | 6/1991 | Dunn et al. | |
| 5,109,430 A | 4/1992 | Nishihara et al. | |
| 5,112,129 A | 5/1992 | Davidson et al. | |
| 5,114,235 A | 5/1992 | Suda et al. | |
| 5,122,660 A | 6/1992 | Yoshii et al. | |
| 5,164,790 A | 11/1992 | McNeil et al. | |
| 5,166,752 A | 11/1992 | Spanier et al. | |
| 5,172,190 A | 12/1992 | Kaiser | |
| 5,182,455 A | 1/1993 | Muraki | |
| 5,182,610 A | 1/1993 | Shibata | |
| 5,189,494 A | 2/1993 | Muraki | |
| 5,216,257 A | 6/1993 | Brueck et al. | |
| 5,316,984 A | 5/1994 | Leourx | |
| 5,327,221 A | 7/1994 | Saitoh et al. | |
| 5,340,992 A | 8/1994 | Matsugu et al. | |
| 5,343,292 A | 8/1994 | Brueck et al. | |
| 5,414,514 A | 5/1995 | Smith et al. | |
| 5,465,148 A | 11/1995 | Matsumoto et al. | |
| 5,479,270 A | 12/1995 | Taylor | |
| 5,525,840 A | 6/1996 | Tominaga | |
| 5,596,406 A | 1/1997 | Rosencwaig et al. | |
| 5,596,413 A | 1/1997 | Stanton et al. | |
| 5,607,818 A | 3/1997 | Akram et al. | |
| 5,608,526 A | 3/1997 | Piwonka-Corle et al. | |
| 5,666,196 A | 9/1997 | Ishii et al. | |
| 5,672,520 A | 9/1997 | Natsume | |
| 5,712,707 A | 1/1998 | Ausschnitt et al. | |
| 5,738,961 A | 4/1998 | Chen | |
| 5,739,909 A | 4/1998 | Blayo et al. | |
| 5,757,507 A | 5/1998 | Ausschnitt et al. | |
| 5,783,342 A | 7/1998 | Yamashita et al. | |
| 5,801,390 A | 9/1998 | Shiraishi | |
| 5,808,742 A | 9/1998 | Everett et al. | |
| 5,872,042 A | 2/1999 | Hsu et al. | |
| 5,877,861 A | 3/1999 | Ausschnitt et al. | |
| 5,883,710 A | 3/1999 | Nikoonahad et al. | |
| 5,889,593 A | 3/1999 | Bareket | |
| 5,902,703 A | 5/1999 | Leroux et al. | |
| 5,903,342 A | 5/1999 | Yatsugake et al. | |
| 5,909,333 A | 6/1999 | Best et al. | |
| 5,910,841 A | 6/1999 | Masao | |
| 5,912,983 A | 6/1999 | Hiratsuka | |
| 5,923,041 A | 7/1999 | Cresswell et al. | |
| 5,939,226 A | 8/1999 | Tomimatu | |
| 5,960,296 A | 9/1999 | Auzino et al. | |
| 5,963,329 A | 10/1999 | Conrad et al. | |
| 6,013,355 A | 1/2000 | Chen et al. | |
| 6,023,338 A | 2/2000 | Bareket | |
| 6,046,094 A | 4/2000 | Jost et al. | |
| 6,077,756 A | 6/2000 | Lin et al. | |
| 6,079,256 A | 6/2000 | Bareket | |
| 6,081,325 A | 6/2000 | Leslie et al. | |
| 6,088,103 A | 7/2000 | Everett et al. | |
| 6,128,089 A | 10/2000 | Ausschnitt et al. | |
| 6,130,750 A | 10/2000 | Ausschnitt et al. | |
| 6,134,011 A | 10/2000 | Klein et al. | |
| 6,153,886 A | 11/2000 | Hagiwara et al. | |
| 6,160,622 A | 12/2000 | Dirksen et al. | |
| 6,165,656 A | 12/2000 | Tomimatu | |
| 6,166,801 A | 12/2000 | Dishon et al. | |
| 6,177,330 B1 | 1/2001 | Yasuda | |
| 6,178,257 B1 | 1/2001 | Alumot et al. | |
| 6,197,679 B1 | 3/2001 | Hattori | |
| 6,255,189 B1 | 7/2001 | Muller et al. | |
| 6,301,001 B1 | 10/2001 | Unno | |
| 6,323,560 B1 | 11/2001 | Narimatsu et al. | |
| 6,342,735 B1 | 1/2002 | Colelli et al. | |
| 6,407,396 B1 | 6/2002 | Mih et al. | |
| 6,420,791 B1 | 7/2002 | Huang et al. | |
| 6,420,971 B1 | 7/2002 | Leck et al. | |
| 6,421,124 B1 | 7/2002 | Matsumoto et al. | |
| 6,429,943 B1 | 8/2002 | Opsal et al. | |
| 6,462,818 B1 | 10/2002 | Bareket | |
| 6,465,322 B2 | 10/2002 | Ziger et al. | |
| 6,476,920 B1 | 11/2002 | Scheiner et al. | |
| 6,486,954 B1 | 11/2002 | Mieher et al. | |
| 6,490,028 B1 | 12/2002 | Ditto et al. | |
| 6,522,406 B1 | 2/2003 | Rovira et al. | |
| 6,561,661 B2 | 5/2003 | Egawa | |
| 6,590,656 B2 | 7/2003 | Xu et al. | |
| 6,594,024 B1 | 7/2003 | Singh et al. | |
| 6,606,152 B2 | 8/2003 | Littau et al. | |
| 6,611,330 B2 | 8/2003 | Lee et al. | |
| 6,633,831 B2 | 10/2003 | Nikoonahad et al. | |
| 6,654,131 B2 | 11/2003 | Opsal et al. | |
| 6,665,070 B1 | 12/2003 | Yarussi et al. | |
| 6,689,519 B2 | 2/2004 | Brown et al. | |
| 6,699,624 B2 | 3/2004 | Niu et al. | |
| 6,699,627 B2 | 3/2004 | Smith et al. | |
| 6,699,630 B2 | 3/2004 | Ota | |
| 6,710,876 B1 | 3/2004 | Nikoonahad et al. | |
| 6,721,052 B2 | 4/2004 | Zhao et al. | |
| 6,772,084 B2 | 8/2004 | Bischoff et al. | |
| 6,804,005 B2 | 10/2004 | Bischoff et al. | |
| 6,819,426 B2 | 11/2004 | Sezginer | |
| 6,822,740 B2 | 11/2004 | Nomura et al. | |
| 6,855,464 B2 | 2/2005 | Niu et al. | |
| 6,856,408 B2 | 2/2005 | Raymond | |
| 7,242,464 B2 | 7/2007 | Hansen | |

(56) References Cited

U.S. PATENT DOCUMENTS

| | | |
|---|---|---|
| 7,751,046 B2 | 7/2010 | Levy et al. |
| 8,525,994 B2 | 9/2013 | Abdulhalim et al. |
| 2001/0019407 A1 | 9/2001 | Sato et al. |
| 2001/0026366 A1 | 10/2001 | Nomura |
| 2001/0030296 A1 | 10/2001 | Ishimaru et al. |
| 2002/0018217 A1 | 2/2002 | Weber-Grabau et al. |
| 2002/0072001 A1 | 6/2002 | Brown et al. |
| 2002/0135875 A1 | 9/2002 | Niu et al. |
| 2002/0149782 A1 | 10/2002 | Raymond |
| 2002/0158193 A1 | 10/2002 | Sezginer et al. |
| 2002/0192577 A1 | 12/2002 | Fay et al. |
| 2003/0002043 A1 | 1/2003 | Abdulhalim et al. |
| 2003/0020184 A1 | 1/2003 | Ballarin |
| 2003/0212525 A1 | 11/2003 | Bischoff et al. |
| 2005/0157297 A1 | 7/2005 | Abdulhalim et al. |
| 2006/0262326 A1 | 11/2006 | Abdulhalim et al. |
| 2007/0127025 A1 | 6/2007 | Abdulhalim et al. |

FOREIGN PATENT DOCUMENTS

| | | |
|---|---|---|
| JP | 60126881 | 7/1985 |
| JP | 63243804 | 10/1988 |
| JP | 09232221 | 9/1997 |
| JP | 11086332 | 3/1999 |
| JP | 2000012459 | 1/2000 |
| JP | 2001272208 | 10/2001 |
| WO | WO-8504266 A1 | 9/1985 |
| WO | WO-9502200 A1 | 1/1995 |
| WO | WO-9945340 A1 | 9/1999 |
| WO | WO-9956174 A1 | 11/1999 |
| WO | WO-0173824 A1 | 10/2001 |
| WO | WO-0184382 A1 | 11/2001 |
| WO | WO-0197279 A2 | 12/2001 |
| WO | WO-0215238 A2 | 2/2002 |
| WO | WO-0218871 A2 | 3/2002 |
| WO | WO-0225708 A2 | 3/2002 |
| WO | WO-0225723 A2 | 3/2002 |
| WO | WO-0235300 A2 | 5/2002 |
| WO | WO-0250509 A2 | 6/2002 |
| WO | WO-02065545 A2 | 8/2002 |
| WO | WO-02069390 A2 | 9/2002 |
| WO | WO-03001297 A2 | 1/2003 |
| WO | WO-03042629 A1 | 5/2003 |
| WO | WO-03054475 A2 | 7/2003 |

OTHER PUBLICATIONS

Auzino et al., "A new technique for multiple overlay check," Microelectric Engineering, vols. 41-42, Match 1998, pp. 607-610 (abstract).

Bae et al., "Performance of new overlay measurement mark," Proceedings of SPIE 2725, May 1996, pp. 424-435.

Baumbach et al., "Grazing Incidence Diffraction by Laterally Patterned Semiconductor Nanostructures," Journal of Physics D: Applied Physics, vol. 32, No. 6, 1999, pp. 726-740 (abstract).

Bischoff et al., "Light Diffraction Based Overlay Measurement," Proceedings SPIE vol. 4344-28, 2001, 12 pages.

Bischoff et al., "Modeling of optical scatterometry with finite-number-of-periods gratings," Proceedings of the SPIE 3743, Apr. 27, 1999, pp. 41-48.

Communication Pursuant to Article 94(3) EPC issued in European Patent Application No. 02 728 700.2 mailed Apr. 9, 2009, 5 pages.

Communication Pursuant to Article 94(3) EPC issued in European Patent Application No. 02 728 700.2 mailed Feb. 1, 2011, 3 pages.

Communication Pursuant to Article 94(3) EPC issued in European Patent Application No. 02 728 700.2 mailed Jan. 23, 2008, 6 pages.

Communication Pursuant to Article 94(3) EPC issued in European Patent Application No. 02 728 700.2 mailed Jun. 18, 2010, 7 pages.

Communication Pursuant to Article 94(3) EPC issued in European Patent Application No. 02 728 700.2 mailed Sep. 26, 2012, 9 pages.

Email Communication regarding U.S. Appl. No. 12/428,401 dated Oct. 5, 2002, 1 page.

European Extended Search Report issued in European Patent Application No. 02 728 700.2 mailed Aug. 13, 2007, 3 pages.

Fattakhov et al., "Formation of Periodic Diffraction Structures at Semiconductor Surfaces for Studying the Dynamics of Photoinduced Phase Transitions," Optics and Spectroscopy, vol. 89, No. 1, 2000, pp. 136-142.

Final Office Action issued in U.S. Appl. No. 10/699,153 mailed Oct. 17, 2008, 6 pages.

Final Office Action issued in U.S. Appl. No. 11/125,590 mailed Feb. 12, 2008, 20 pages.

Final Office Action issued in U.S. Appl. No. 11/125,590 mailed Sep. 22, 2008 12 pages.

Final Office Action issued in U.S. Appl. No. 11/281,820 mailed Sep. 10, 2008, 16 pages.

Final Office Action issued in U.S. Appl. No. 11/495,001 mailed Mar. 20, 2009, 14 pages.

Final Office Action issued in U.S. Appl. No. 11/673,115 mailed Aug. 15, 2008, 9 pages.

Final Office Action issued in U.S. Appl. No. 12/428,401, mailed Jun. 24, 2011, 13 pages.

IBM Technical Disclosure Bulletin, "Interferometic Measurement System for Overlay Measurement in Lithographic Processes," IBM Technical Disclosure Bulletin, Feb. 1994, pp. 535-536.

IBM Technical Disclosure Bulletin, "Mask Overlay Determination," IBM Technical Disclosure Bulletin, Dec. 1978, pp. 2772-2773.

IBM Technical Disclosure Bulletin, "Phase-Sensitive Overlay Analysis Spectrometry," IBM Technical Disclosure Bulletin, Mar. 1990, pp. 170-174.

IBM Technical Disclosure Bulletin, "Width and Overlay Narrow Kerf Test Site," IBM Technical Disclosure Bulletin, Apr. 1978, pp. 4357-4358.

Ina et al., "Alignment Mark Optimization to Reduce Tool- and Wafer-Induced Shift for XRA-1000," Japanese Journal of Applied Physics, vol. 38, Part 1, No. 12B, Dec. 1999, pp. 7065-7070 (abstract).

International Search Report issued in International Patent Application No. PCT/US2002/011026 mailed Sep. 18, 2002, 4 pages.

Invitation Pursuant to Article 94(3) and Rule 71(1) EPC issued in European Patent Application No. 07 728 700.2, mailed Feb. 14, 2014, including copies of emails sent by examiner and representative, 19 pages.

Kim et al., "Automatic in-situ focus monitor using line-shortening effect," Proc. SPIE 3677, Metrology, Inspection, and Process Control for Microlithography XIII, Jun. 14, 1999, pp. 184-193 (abstract).

Kleinknecht, "Diffraction and interference optics for monitoring fine dimensions in device manufacture," European Solid State Device Research Conference and Eight Symposium on Solid State Device Technology, Sep. 13-16, 1983, pp. 29-44 (abstract).

Kodate et al., "Towards the Optimal Design of Binary Optical Elements with Different Phase Levels Using a Method of Phase Mismatch Correction," Trends in Optics and Photonics, vol. 41, 2002, pp. 174-176.

Levinson et al., "Minimization of total overlay errors on product wafers using an advanced optimization scheme," Proceedings of the APIE 3051, 1997, pp. 362-373.

Levinson, "Lithography Process Control," Tutorial Texts in Optical Engineering, SPIE Press vol. TT28, Chapter 5: Overlay, 1999, 37 pages.

Li, "A Modal Analysis of Lamellar Diffraction Gratings in Conical Mountings," Journal of Modern Optics, 1993, vol. 40, No. 4, pp. 553-573.

List of Claims for European Application No. 02 728 700.2 filed Apr. 9, 2002, 4 pages.

Moharam et al., "Rigorous coupled-wave analysis of planar-grating diffraction," Journal of the Optical Society of America, vol. 71, No. 7, Jul. 1981, pp. 811-818.

Non-Final Office Action issued in U.S. Appl. No. 12/428,401 mailed Oct. 14, 2010, 24 pages.

Non-Final Office Action issued in U.S. Appl. No. 10/699,153 mailed Jan. 17, 2008, 25 pages.

(56) References Cited

OTHER PUBLICATIONS

Non-Final Office Action issued in U.S. Appl. No. 11/281,820 mailed Nov. 14, 2007, 16 pages.
Non-Final Office Action issued in U.S. Appl. No. 11/495,001 mailed Jun. 4, 2008, 11 pages.
Non-Final Office Action issued in U.S. Appl. No. 11/495,001 mailed Sep. 2, 2009 9 pages.
Non-Final Office Action issued in U.S. Appl. No. 11/673,115 mailed Feb. 29, 2008, 20 pages.
Non-Final Office Action issued in U.S. Appl. No. 12/428,401, mailed on Oct. 18, 2012, 11 pages.
Non-Final Office Action issued in U.S. Appl. No. 14/035,766 mailed Oct. 1, 2014, 6 pages.
Notice of Allowance and Fees Due issued in U.S. Appl. No. 12/428,401, mailed on May 1, 2013, 9 pages.
Notice of Allowance issued in U.S. Appl. No. 14/035,766 mailed Mar. 25, 2015, 8 pages.
Notice of Allowance issued in U.S. Appl. No. 14/789,796 mailed Sep. 18, 2015, 14 pages.
Notification of Reasons for Refusal issued in Japanese Patent Application No. 2002-581921 mailed Apr. 7, 2009, 3 pages.
Notification of Reasons for Refusal issued in Japanese Patent Application No. 2002-581921 mailed Mar. 18, 2008, 5 pages.
Papazoglou et al., "Photorefractive optical properties of volume phase gratings induced in sillenite crystals, when the grating vector lies on the (111) plane," Appl. Phys. B, vol. 7, 2000, pp. 841-848.
Pelligrini et al., "Super Sparse Overlay Sampling Plans: An Evaluation of Methods and Algorithms for Optimizing Overlay Quality Control and Metrology Tool Throughput," Proceedings of SPIE 3677, Mar. 1999, pp. 72-82.
Pforr et al., "In-process image detection technique for determination of overlay and image quality for ASM-L wafer stepper," Proc. SPIE 1674, Optical/Laser Microlithography V, Jun. 1, 1992, pp. 594-608 (Abstract Not Available).
Prakash et al., "Comparison of optical, SEM, and AFM overlay measurement," Proc. SPIE 3677, Metrology, Inspection, and Process Control for Microlithography XIII, Jun. 14, 1999, pp. 229-238 (abstract).
Rangarajan et al., "Optimal Sampling Strategies for sub-100 nm Overlay," Proceedings of the SPIE 3332, 1998, pp. 348-359.
Schmidt et al., "Interferometric Method of Checking the Overlay Accuracy in Photolithographic Exposure Processes," IBM Technical Disclosure Bulletin, Mar. 1990, pp. 214-217.
Sheng et al., "Exact Eigenfunctions for Square-Wave Gratings: Application to Diffraction and Surface-Plasmon Calculations," Physical Review B, vol. 26, No. 6, Sep. 15, 1982, pp. 2907-2916 (abstract).
Sherman et al., "Characterization and monitoring of variable NA and variable coherence capable photosteppers utilizing the phase shift focus monitor reticle," Proc. SPIE 2439, Integrated Circuit Methodology, Inspection, and Process Control IX, May 22, 1995, pp. 61-69 (abstract).
Tobin, Jr. et al., "Automatic classification of spatial signatures on semiconductor wafer maps," Proc. SPIE, Metrology, Inspection, and Process Control for Microlithography XI, Jul. 7, 1997, 434-444 (abstract).
Uchida et al., "A mask-to-wafer alignment and gap setting method for x-ray lithography using gratings," Journal of Vacuum Science & Technology B, vol. 9, 1991, p. 3202-3206 (abstract).
Written Opinion of the IPEA issued in International Patent Application No. PCT/US2002/11206 mailed Apr. 11, 2003, 4 pages.

\* cited by examiner

PERIODIC PATTERNS AND TECHNIQUE TO CONTROL MISALIGNMENT BETWEEN TWO LAYERS

CROSS-REFERENCE TO RELATED APPLICATIONS

This application is a continuation of U.S. application Ser. No. 14/789,796, filed Jul. 1, 2015, which is a continuation of U.S. application Ser. No. 14/035,766, filed Sep. 24, 2013, now U.S. Pat. No. 9,103,662, which is a continuation of U.S. application Ser. No. 12/628,092, filed Nov. 30, 2009, now U.S. Pat. No. 8,570,515, which is a continuation of U.S. application Ser. No. 12/428,401, filed Apr. 22, 2009, now U.S. Pat. No. 8,525,994; which is a continuation of U.S. application Ser. No. 11/495,001, filed Jul. 27, 2006, now abandoned; which is a continuation of application Ser. No. 11/355,613, filed Feb. 15, 2006, now abandoned; which is a continuation of application Ser. No. 11/062,255, filed Feb. 18, 2005, now abandoned; which is a continuation of application Ser. No. 10/682,544, filed Oct. 8, 2003, now abandoned; which is a continuation of application Ser. No. 09/833,084, filed Apr. 10, 2001, now abandoned; which applications are incorporated herein by reference.

BACKGROUND OF THE INVENTION

The invention relates in general to metrology systems for measuring periodic structures such as overlay targets, and, in particular, to a metrology system employing diffracted light for detecting misalignment of such structures.

Overlay error measurement requires specially designed marks to be strategically placed at various locations, normally in the scribe line area between dies, on the wafers for each process. The alignment of the two overlay targets from two consecutive processes is measured for a number of locations on the wafer, and the overlay error map across the wafer is analyzed to provide feedback for the alignment control of lithography steppers.

A key process control parameter in the manufacturing of integrated circuits is the measurement of overlay target alignment between successive layers on a semiconductor wafer. If the two overlay targets are misaligned relative to each other, then the electronic devices fabricated will malfunction, and the semiconductor wafer will need to be reworked or discarded.

Measurement of overlay misregistration between layers is being performed today with optical microscopy in different variations: brightfield, darkfield, confocal, and interference microscopy, as described in Levinson, "Lithography Process Control," chapter 5, SPIE Press Vol. TT28, 1999. Overlay targets may comprise fine structures on top of the wafer or etched into the surface of the wafer. For example, one overlay target may be formed by etching into the wafer, while another adjacent overlay target may be a resist layer at a higher elevation over the wafer. The target being used for this purpose is called box-in-box where the outer box, usually 10 to 30 µm, represents the position of the bottom layer, while the inner box is smaller and represents the location of the upper layer. An optical microscopic image is grabbed for this target and analyzed with image processing techniques. The relative location of the two boxes represents what is called the overlay misregistration, or the overlay. The accuracy of the optical microscope is limited by the accuracy of the line profiles in the target, by aberrations in the illumination and imaging optics and by the image sampling in the camera. Such methods are complex and they require full imaging optics. Vibration isolation is also required.

These techniques suffer from a number of drawbacks. First, the grabbed target image is highly sensitive to the optical quality of the system, which is never ideal. The optical quality of the system may produce errors in the calculation of the overlay misregistration. Second, optical imaging has a fundamental limit on resolution, which affects the accuracy of the measurement. Third, an optical microscope is a relatively bulky system. It is difficult to integrate an optical microscope into another system, such as the end of the track of a lithographic stepper system. It is desirable to develop an improved system to overcome these drawbacks.

SUMMARY OF THE INVENTION

A target for determining misalignment between two layers of a device has two periodic structures of lines and spaces on the two different layers of a device. The two periodic structures overlie or are interlaced with each other. The layers or periodic structures may be at the same or different heights. In one embodiment, either the first periodic structure or the second periodic structure has at least two sets of interlaced grating lines having different periods, line widths or duty cycles. The invention also relates to a method of making overlying or interlaced targets.

An advantage of the target is the use of the same diffraction system and the same target to measure critical dimension and overlay misregistration. Another advantage of the measurement of misregistration of the target is that it is free from optical asymmetries usually associated with imaging.

The invention also relates to a method of detecting misalignment between two layers of a device. The overlying or interlaced periodic structures are illuminated by incident radiation. The diffracted radiation from the overlying or interlaced periodic structures is used to provide an output signal. In one embodiment, a signal is derived from the output signal. The misalignment between the structures is determined from the output signal or the derived signal. In one embodiment, the output signal or the derived signal is compared with a reference signal. A database that correlates the misalignment with data related to diffracted radiation can be constructed.

An advantage of this method is the use of only one incident radiation beam. Another advantage of this method is the high sensitivity of zero-order and first-order diffracted light to the overlay misregistration between the layers. In particular, properties which exhibited high sensitivity are intensity, phase and polarization properties of zero-order diffraction; differential intensity between the positive and negative first-order diffraction; differential phase between the positive and negative first-order diffraction; and differential polarization between the positive and negative first-order diffraction. These properties also yielded linear graphs when plotted against the overlay misalignment. This method can be used to determine misalignment on the order of nanometers.

In one embodiment, a neutral polarization angle, defined as an incident polarization angle where the differential intensity is equal to zero for all overlay misregistrations, is determined. The slope of differential intensity as a function of incident polarization angle is highly linear when plotted against the overlay misregistration. This linear behavior reduces the number of parameters that need to be determined and decreases the polarization scanning needed. Thus, the method of detecting misalignment is faster when using the slope measurement technique.

The invention also relates to an apparatus for detecting misalignment of overlying or interlaced periodic structures. The apparatus comprises a source, at least one analyzer, at least one detector, and a signal processor to determine misalignment of overlying or interlaced periodic structures.

BRIEF DESCRIPTION OF THE DRAWINGS

FIGS. 2b and 2c are top views of the two overlying periodic structures of FIG. 2a.

For simplicity of description, identical components are labeled by the same numerals in this application.

DETAILED DESCRIPTION OF THE EMBODIMENTS

Figure 2A:
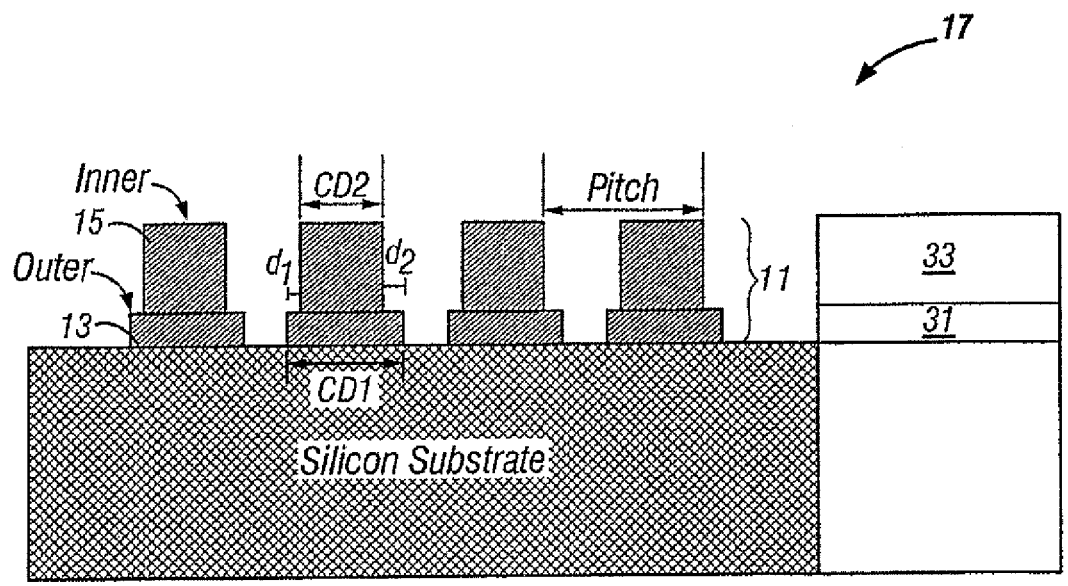
FIG. 2a is a cross-sectional view of two overlying periodic structures.

FIG. 2a is a cross-sectional view of a target 11 comprising two periodic structures 13, 15 on two layers 31, 33 of a device 17. The second periodic structure 15 is overlying or interlaced with the first periodic structure 13. The layers and the periodic structures may be at the same or different heights. The device 17 can be any device of which the alignment between two layers, particularly layers having small features on structures, needs to be determined. These devices are typically semiconductor devices; thin films for magnetic heads for data storage devices such as tape recorders; and flat panel displays.

Figure 1A:
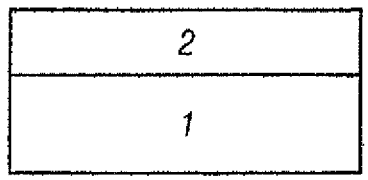
FIGS. 1a-1h are cross-sectional views illustrating basic process steps in semiconductor processing.
Figure 1B:
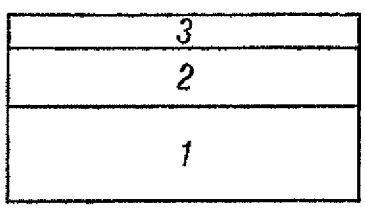
Figure 1C:
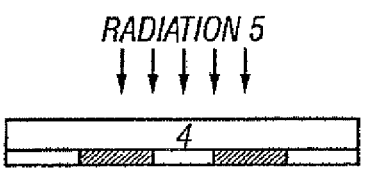
Figure 1D:
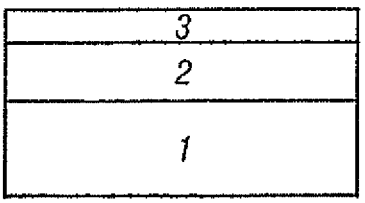
Figure 1E:
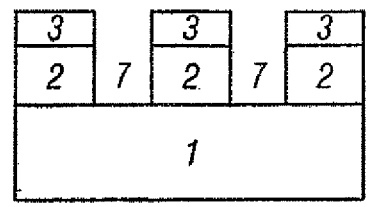
Figure 1F:
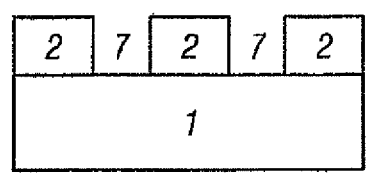
Figure 1G:
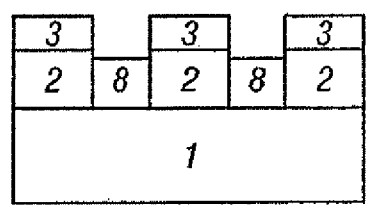
Figure 1H:
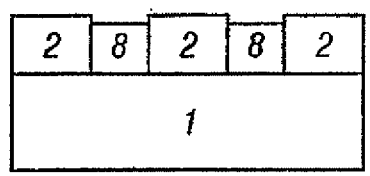

As shown in FIGS. 1a-1h, a device 17 is generally formed in a basic series of steps for each layer. First, as shown in FIG. 1a, a layer 2 is formed on a semiconductor substrate 1. The layer 2 may be formed by oxidization, diffusion, implantation, evaporation, or deposition. Second, as shown in FIG. 1b, resist 3 is deposited on the layer 2. Third, as shown in FIG. 1c, the resist 3 is selectively exposed to a form of radiation 5. This selective exposure is accomplished with an exposure tool and mask 4, or data tape in electron or ion beam lithography (not shown). Fourth, as shown in FIG. 1d, the resist 3 is developed. The resist 3 protects the regions 6 of the layer 2 that it covers. Fifth, as shown in FIG. 1e, the exposed regions 7 of the layer 2 are etched away. Sixth, as shown in FIG. 1f, the resist 3 is removed. Alternatively, in another embodiment, another material 8 can be deposited in the spaces 7, as shown in FIG. 1e, of the etched layer 2, as shown in FIG. 1g, and the resist 3 is removed after the deposition, as shown in FIG. 1h. This basic series of steps is repeated for each layer until the desired device is formed.

A first layer 31 and a second layer 33 can be any layer in the device. Unpatterned semiconductor, metal or dielectric layers may be deposited or grown on top of, underneath, or between the first layer 31 and the second layer 33.

The pattern for the first periodic structure 13 is in the same mask as the pattern for a first layer 31 of the device, and the pattern for the second periodic structure 15 is in the same mask as the pattern for a second layer 33 of the device. In one embodiment, the first periodic structure 13 or the second periodic structure 15 is the etched spaces 7 of the first layer 31 or the second layer 33, respectively, as shown in FIG. 1f. In another embodiment, the first periodic structure 13 or the second periodic structure 15 is the lines 2 of the first layer 31 or the second layer 33, respectively, as shown in FIG. 1f. In another embodiment, the first periodic structure 13 or the second periodic structure 15 is another material 8 deposited in the spaces 7 of the first layer 31 or the second layer 33, respectively, as shown in FIG. 1h. In yet another embodiment, the second layer 33 is resist, and the second periodic structure 15 is resist 3 gratings, as shown in FIG. 1d.

The first periodic structure 13 has the same alignment as the first layer 31, since the same mask was used for the pattern for the first periodic structure 13 and for the pattern for the first layer 31. Similarly, the second periodic structure 15 has the same alignment as the second layer 33. Thus, any overlay misregistration error in the alignment between the first layer 31 and the second layer 33 will be reflected in the alignment between the first periodic structure 13 and the second periodic structure 15.

Figure 2B:
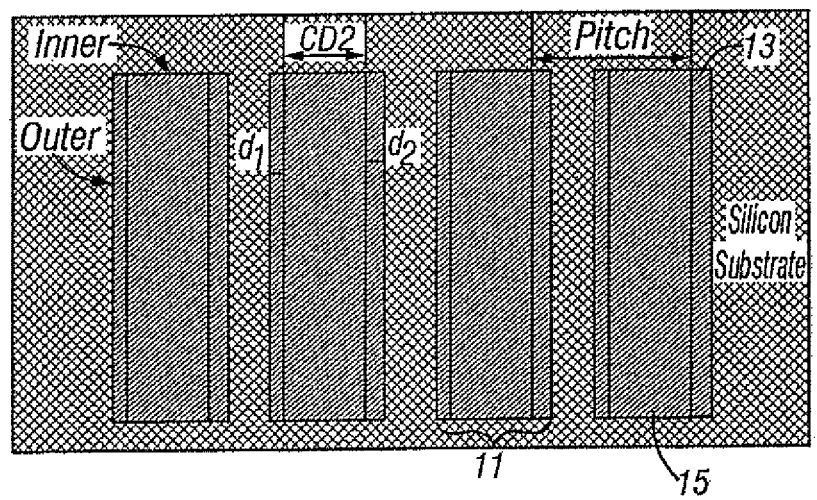
Figure 2C:
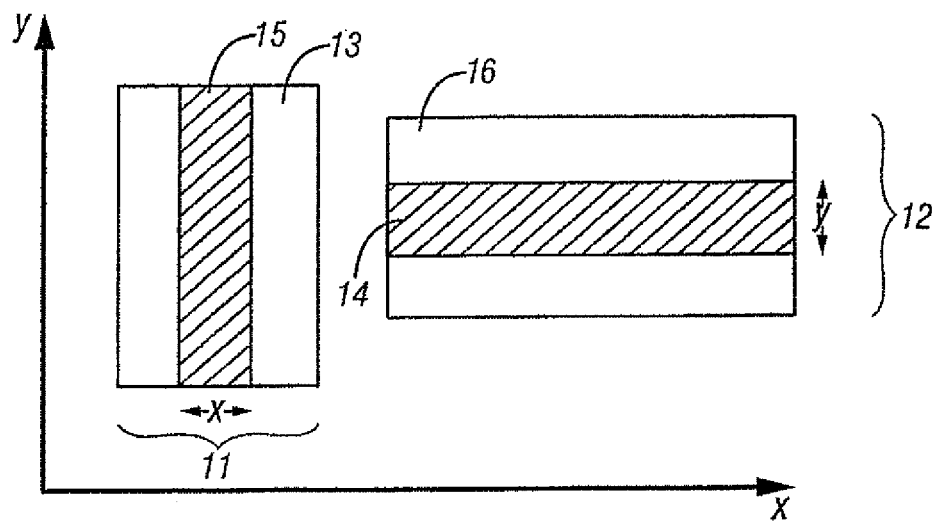

FIGS. 2b and 2c are top views of target 11. In one embodiment, as illustrated in FIG. 2a, the first periodic structure 13 has a first selected width CD1, and the second periodic structure 15 has a second selected width CD2. The second selected width CD2 is less than the first selected width CD1. The pitch, also called the period or the unit cell, of a periodic structure is the distance after which the pattern is repeated. The distance between the left edge of the first periodic structure 13 and the left edge of the second periodic structure 15 is $d_1$, and the distance between the right edge of the first periodic structure 13 and the right edge of the second periodic structure 15 is $d_2$. In a preferred embodiment, when layers 31, 33 are properly aligned relative to each other, the second periodic structure 15 is centered over the first periodic structure 13. In other words, when the second periodic structure 15 is perfectly centered over the first periodic structure 13, the misregistration is zero, and $d_1=d_2$. In this embodiment, the misregistration is indicated by $d_2-d_1$. To obtain misregistration in both the X and Y directions of the XY coordinate system, another target 12 comprising two periodic structures 14, 16 similar to target 11 is placed substantially perpendicular to target 11, as shown in FIG. 2c.

The target 11 is particularly desirable for use in photolithography, where the first layer 31 is exposed to radiation for patterning purposes of a semiconductor wafer and the second layer 33 is resist. In one embodiment, the first layer 31 is etched silicon, and the second layer 33 is resist.

Figure 4A:
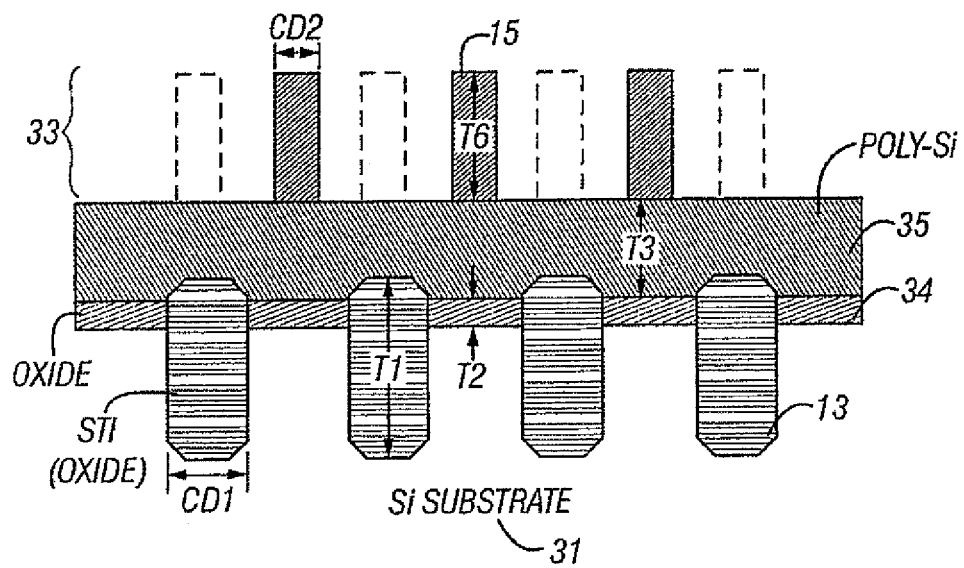
FIGS. 4a and 4b are cross-sectional views of overlying or interlaced periodic structures illustrating other embodiments of the invention.
Figure 4B:
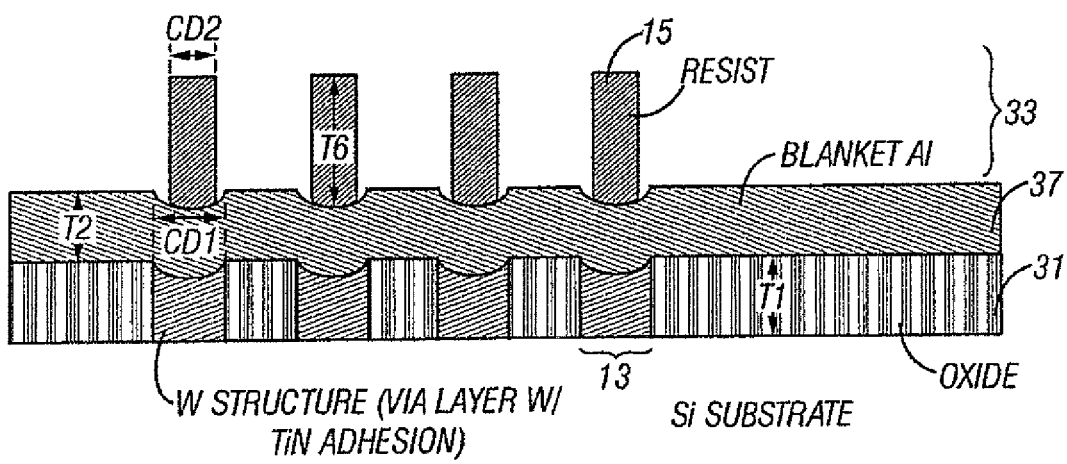

FIGS. 4a and 4b show alternative embodiments. In one embodiment, FIG. 4a illustrates a first periodic structure 13 of oxide having a trapezoidal shape on a first layer 31 of silicon substrate and a second periodic structure 15 of resist with a second layer 33 of resist. The first layer 31 of silicon is etched, and shallow trench isolation ("STI") oxide is deposited in the spaces of the etched silicon. The lines of STI oxide form the first periodic structure 13. An oxide layer 34 and a uniform polysilicon layer 35 are deposited between the first layer 31 of silicon and the second layer 33 of resist. The configuration in FIG. 4a shows a line on space configuration, where the second periodic structure 15 is placed aligned with the spaces between the first periodic structure 13. The invention also encompasses embodiments such as the line on line configuration, where the lines in the second periodic structure 15 are placed on top of and aligned with the lines in the first periodic structure 13, as shown by the dotted lines in FIG. 4a.

In another embodiment, FIG. 4b illustrates a first periodic structure 13 of tungsten etched in a first layer 31 of oxide and a second periodic structure 15 of resist with a second layer 33 of resist. The first layer 31 and the second layer 33 are separated by an aluminum blanket 37.

The invention relates to a method of making a target 11. A first periodic structure 13 is placed over a first layer 31 of a device 17. A second periodic structure 15 is placed over a second layer 33 of the device 17. The second periodic structure 15 is overlying or interlaced with the first periodic structure 13.

In one embodiment, another target 12 is placed substantially perpendicular to target 11, as shown in FIG. 2c. A third periodic structure 14 is placed over the first layer 31, and a fourth periodic structure 14 is placed over the second layer 33. The third periodic structure 14 is substantially perpendicular to the first periodic structure 13, and the fourth periodic structure 16 is substantially perpendicular to the second periodic structure 15.

Figure 3:
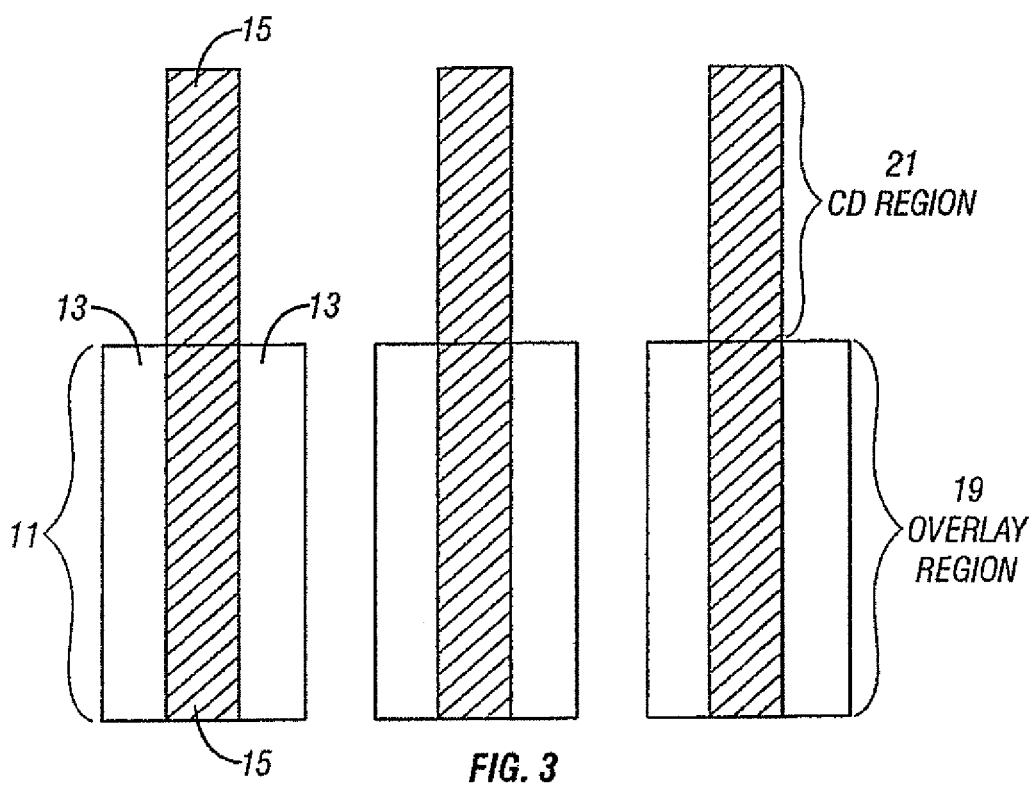
FIG. 3 is a top view of two overlying periodic structures illustrating an embodiment of the invention.

An advantage of the target 11 is that the measurement of misregistration of the target is free from optical asymmetries usually associated with imaging. Another advantage of this measurement is that it does not require scanning over the target as it is done with other techniques, such as in Bareket, U.S. Pat. No. 6,023,338. Another advantage of the target 11 is the elimination of a separate diffraction system and a different target to measure the critical dimension ("CD") of a periodic structure. The critical dimension, or a selected width of a periodic structure, is one of many target parameters needed to calculate misregistration. Using the same diffraction system and the same target to measure both the overlay misregistration and the CD is more efficient. The sensitivity associated with the CD and that with the misregistration is distinguished by using an embodiment of a target as shown in FIG. 3. The second periodic structure 15 extends further to an area, the CD region 21, where the first periodic structure 13 does not extend. The first selected width CD1 is measured before placing the second periodic structure 15 on the device 17. After forming the target, the second selected width CD2 alone can be measured in the CD region 21. In a separate measurement, the misregistration is determined in an overlay region 19 where both the first 13 and second 15 periodic structures lie.

Figure 5A:
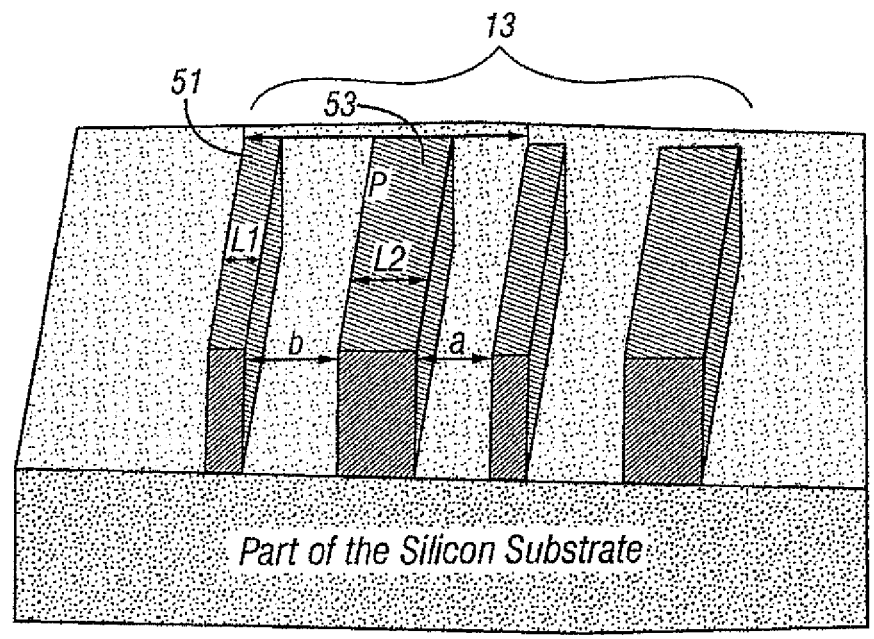
FIGS. 5a and 5b are cross-sectional views of two interlaced periodic structures illustrating interlaced gratings in an embodiment of the invention.
Figure 5B:
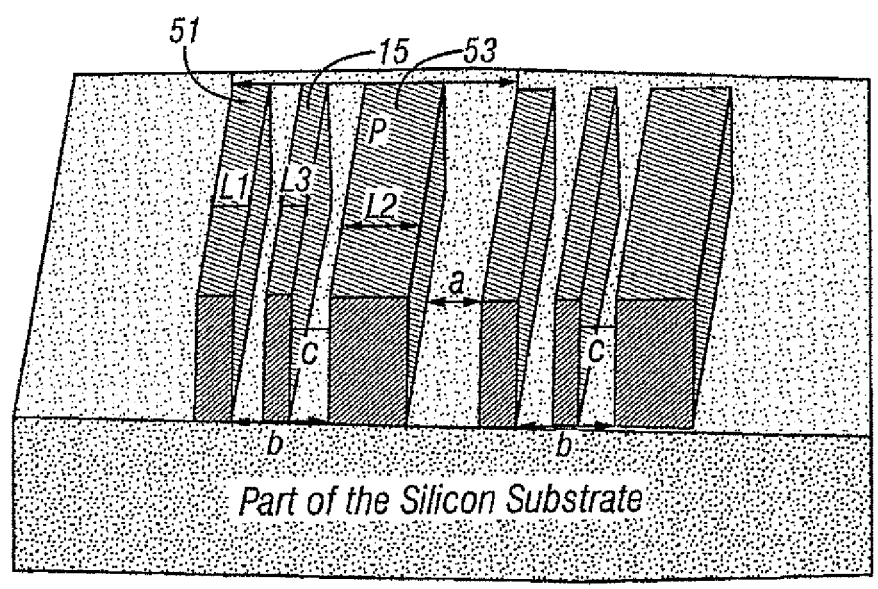

FIGS. 5a and 5b are cross-sectional views of an embodiment of a target having interlaced gratings. The first periodic structure 13 or the second periodic structure 15 has at least two interlaced grating lines having different periods, line widths or duty cycles. The first periodic structure 13 is patterned with the same mask as that for the first layer 31, and the second periodic structure 15 is patterned with the same mask as that for the second layer 33. Thus, the first periodic structure 13 has the same alignment as the first layer 31, and the second periodic structure 15 has the same alignment as the second layer 33. Any misregistration between the first layer 31 and the second layer 33 is reflected in the misregistration between the first periodic structure 13 and the second periodic structure 15.

In the embodiment shown in FIGS. 5a and 5b, the first periodic structure 13 has two interlaced grating lines 51, 53. The first interlaced grating lines 51 have a line-width $L_1$, and the second interlaced grating lines 53 have a line-width $L_2$. The second periodic structure 15, as shown in FIG. 5b, has a line-width $L_3$ and is centered between the first interlaced grating lines 51 and the second interlaced grating lines 53. The distance between the right edge of the first interlaced grating 51 and the adjacent left edge of the second interlaced grating 53 is represented by b, and the distance between the right edge of the second periodic structure 15 and the adjacent left edge of the second interlaced grating 53 is represented by c. The misregistration between the first layer 31 and the second layer 33 is equal to the misregistration ∈ between the first periodic structure 13 and the second periodic structure 15. The misregistration ∈ is:

$$\varepsilon = \frac{b}{2} - \frac{L_3}{2} - c \tag{1}$$

Where c=0, the resulting periodic structure has the most asymmetric unit cell composed of a line with width of $L_2+L_3$ and a line with width $L_1$. Where $c=b-L_3$, the resulting periodic structure has the most symmetric unit cell composed of a line with width $L_1+L_3$ and a line with width $L_2$. For example, if the two layers are made of the same material and $L_1=L_3=L_2/2$, then the lines are identical where c=0, while one line is twice as wide as the other line where $c=b-L_3$.

Figure 6:
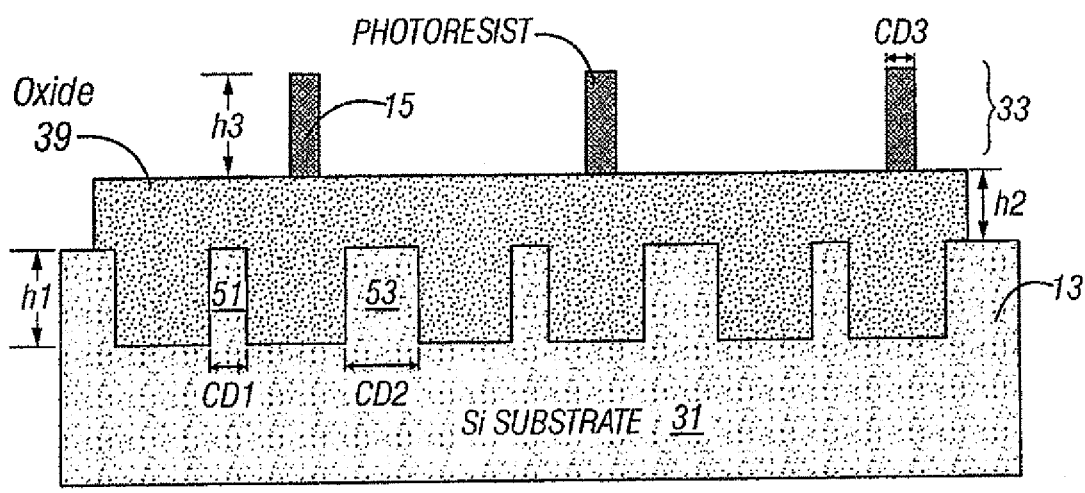
FIG. 6 is a cross-sectional view of two interlaced periodic structures illustrating interlaced gratings in another embodiment of the invention.

FIG. 6 shows an alternative embodiment of a target having interlaced gratings. The first periodic structure 13 is etched silicon, and the second periodic target 15 is resist. The first layer 31 of silicon substrate and the second layer 33 of resist are separated by an oxide layer 39.

The invention also relates to a method of making a target 11. A first periodic structure 13 is placed over a first layer 31 of a device 17. A second periodic structure 15 is placed over a second layer 33 of the device 17. The second periodic structure 15 is overlying or interlaced with the first periodic structure 13. Either the first periodic structure 13 or the second periodic structure 15 has at least two interlaced grating lines having different periods, line widths or duty cycles.

Figures 7A, 7B:
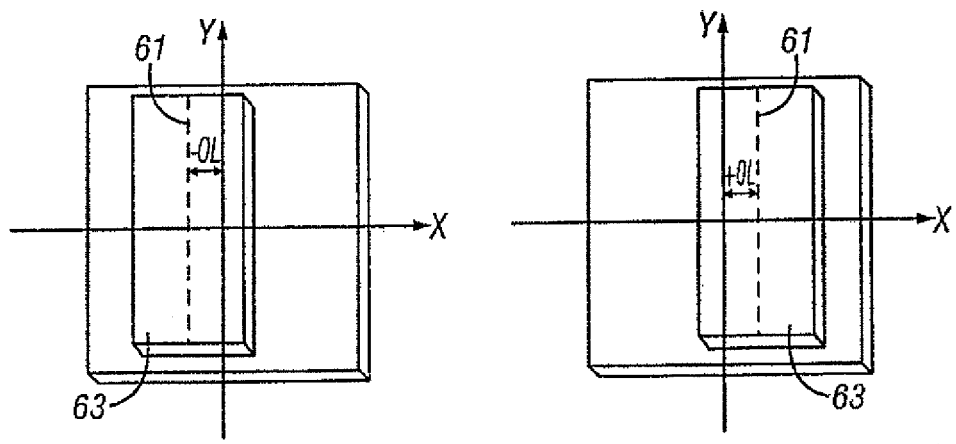
FIGS. 7a and 7b are schematic views illustrating negative and positive overlay shift, respectively.

An advantage of interlaced gratings is the ability to determine the sign of the shift of the misregistration from the symmetry of the interlaced gratings. FIGS. 7a and 7b are schematic drawings illustrating negative and positive overlay shift, respectively, in the X direction of the XY coordinate system. Center line 61 is the center of a grating 63. When the grating 63 is aligned perfectly, the center line 61 is aligned with the Y axis of the XY coordinate system. As shown in FIG. 7a, a negative overlay shift is indicated by the center line 61 being in the negative X direction. As shown in FIG. 7b, a positive overlay shift is indicated by the center line 61 being in the positive X direction. The negative overlay shift is indicated by a negative number for the misregistration, and the positive overlay shift is indicated by a positive number for the misregistration. The misregistration can be determined using the method discussed below. In the case of the interlaced gratings, a negative overlay shift results in a more symmetrical unit cell, as where $c=b-L_3$, discussed above. A positive overlay shift results in a more asymmetrical unit cell, as where $c=0$, discussed above.

Figure 8:
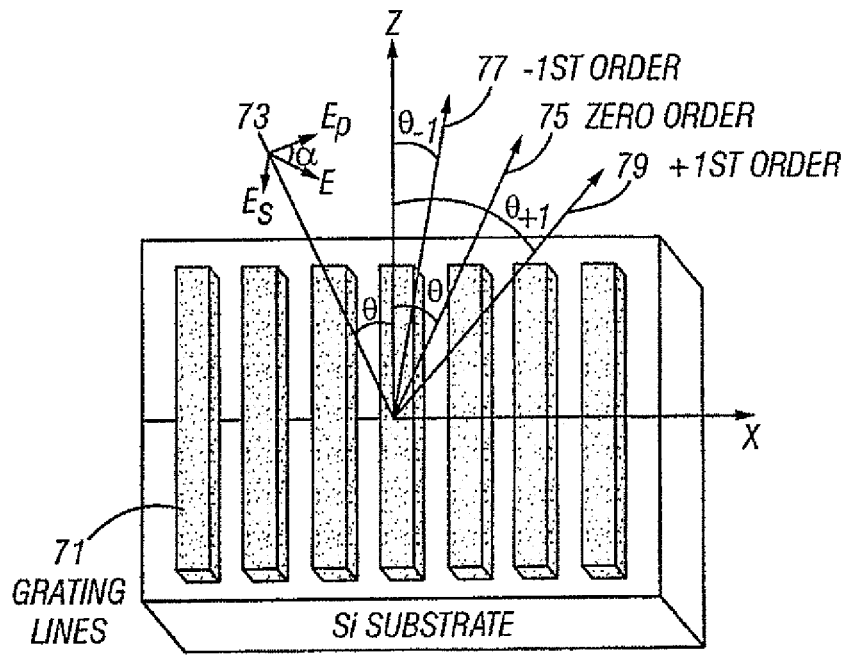
FIG. 8 is a schematic view illustrating the diffraction of light from a grating structure.

The invention relates to a method to determine misalignment using diffracted light. FIG. 8 is a schematic view showing the diffraction of light from a grating structure 71. In one embodiment, incident radiation 73 having an oblique angle of incidence θ illuminates the grating structure 71. The grating structure 71 diffracts radiation 75, 77, 79. Zero-order diffraction 75 is at the same oblique angle θ to the substrate as the incident radiation 73. Negative first-order diffraction 77 and positive first-order diffraction 79 are also diffracted by the grating structure 71.

Figure 9A:
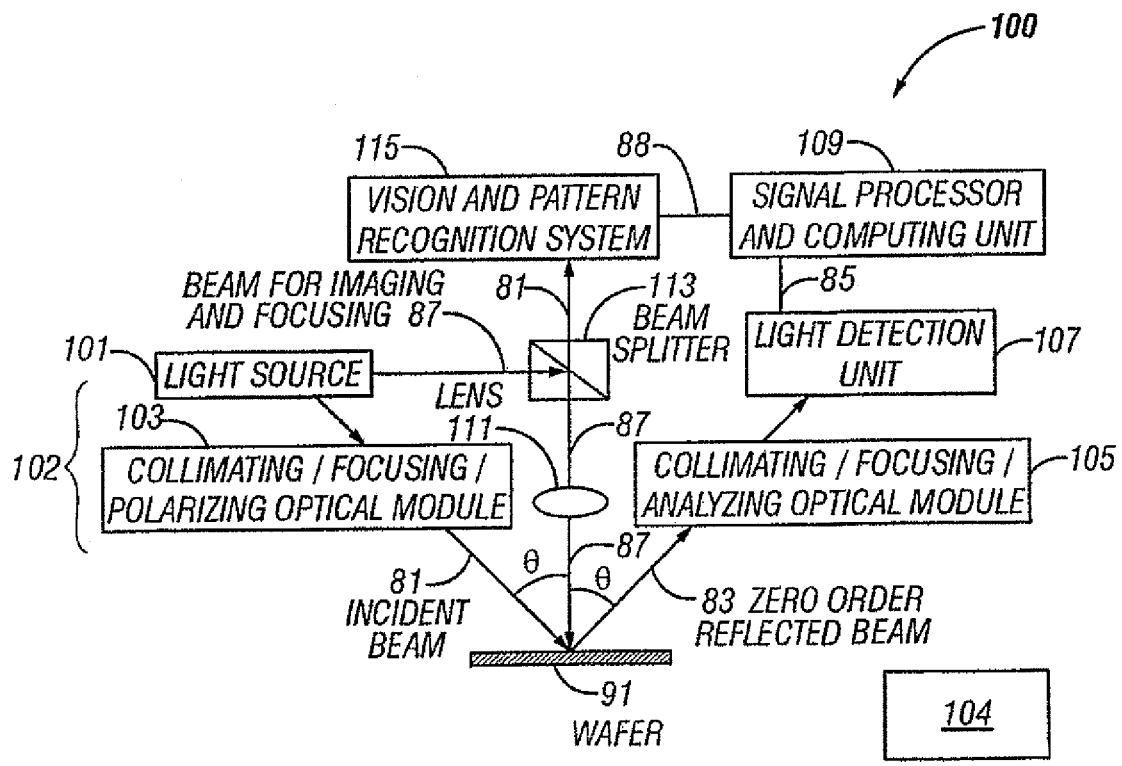
FIG. 9a is a schematic block diagram of an optical system that measures zero-order diffraction from overlying or interlaced periodic structures.
Figure 10A:
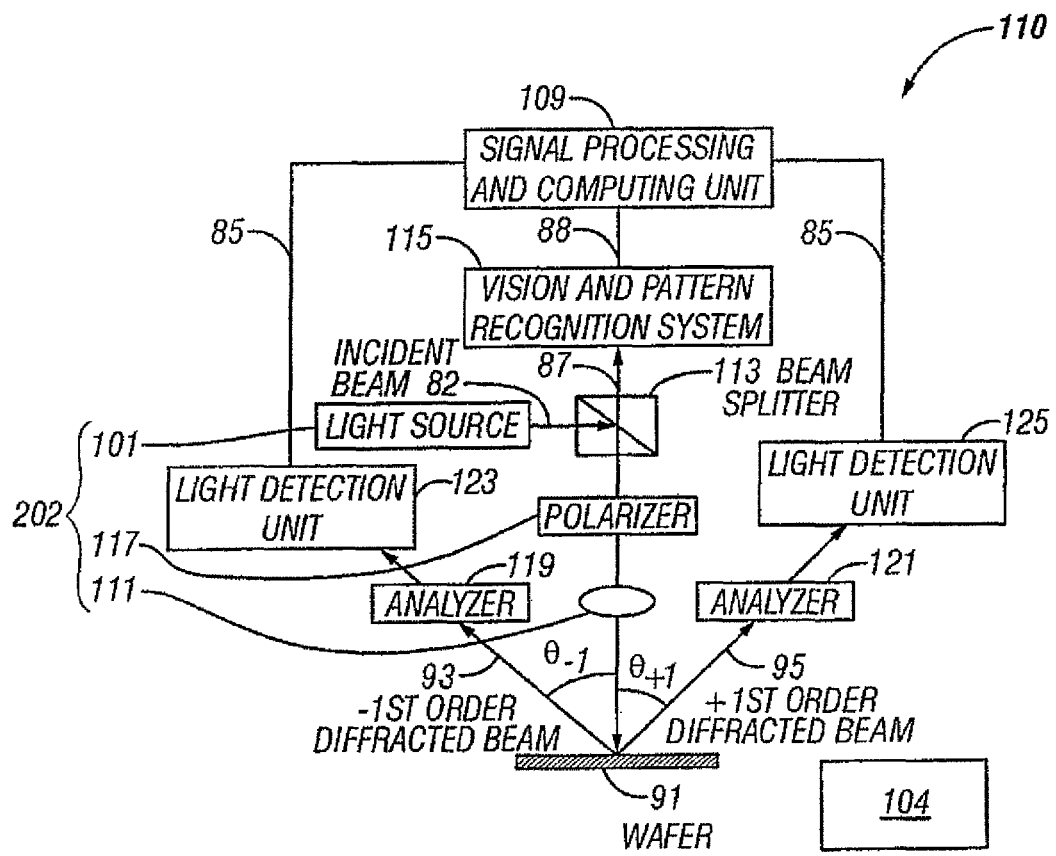
FIGS. 10a and 11a are schematic block diagrams of an optical system that measures first-order diffraction from a normal incident beam on overlying or interlaced periodic structures.
Figure 11A:
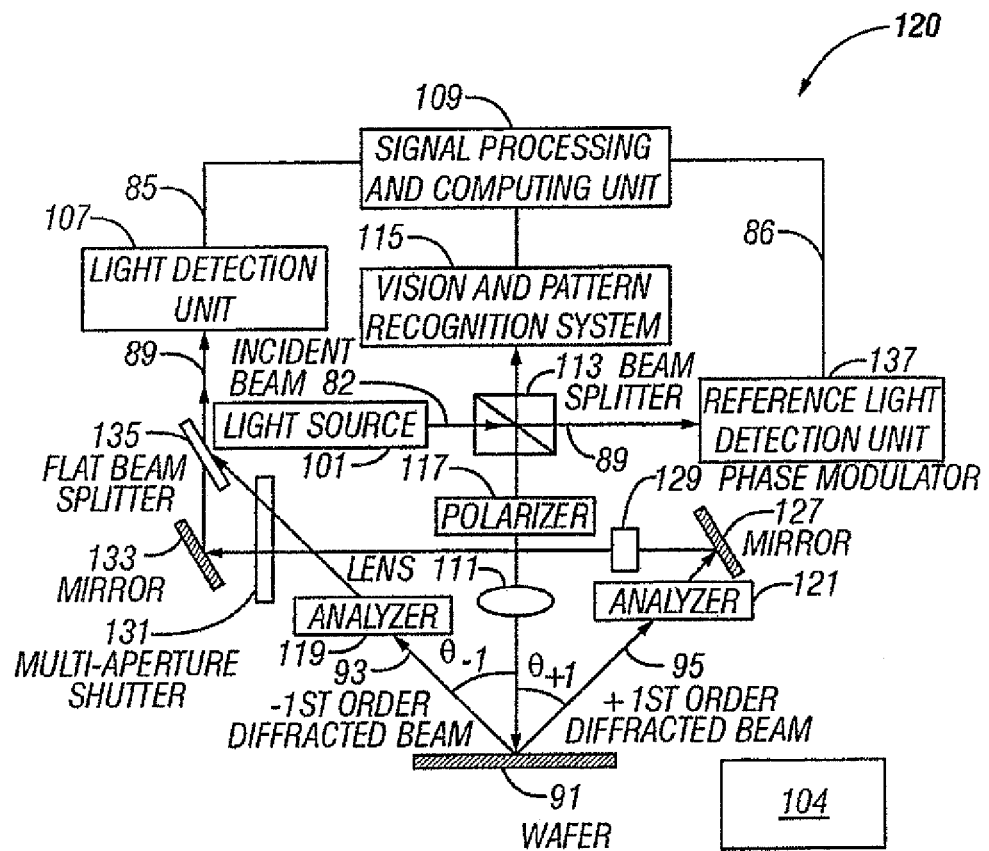

Optical systems for determining misalignment of overlying or interlaced periodic structures are illustrated in FIGS. 9a, 10a, and 11a. FIG. 9a shows an optical system 100 using incident radiation beam 81 with an oblique angle of incidence and detecting zero-order diffracted radiation 83. A source 102 provides polarized incident radiation beam 81 to illuminate periodic structures on a wafer 91. The incident radiation beam may be substantially monochromatic or polychromatic. The source 102 comprises a light source 101 and optionally a collimating/focusing/polarizing optical module 103. The structures diffract zero-order diffracted radiation 83. A collimating/focusing/analyzing optical module 105 collects the zero-order diffracted radiation 83, and a light detection unit 107 detects the zero-order diffracted radiation 83 collected by the analyzer in module 105 to provide an output signal 85. A signal processor 109 determines any misalignment between the structures from the output signal 85. The output signal 85 is used directly to determine misalignment from the intensity of the zero-order diffracted radiation 83. In a preferred embodiment, the misalignment is determined by comparing the intensity with a reference signal, such as a reference signal from a calibration wafer or a database, compiled as explained below. In one embodiment, the signal processor 109 calculates a derived signal from the output signal 85 and determines misalignment from the derived signal. The derived signal can include polarization or phase information. In this embodiment, the misalignment is determined by comparing the derived signal with a reference signal.

In one embodiment, optical system 100 provides ellipsometric parameter values, which are used to derive polarization and phase information. In this embodiment, the source 102 includes a light source 101 and a polarizer in module 103. Additionally, a device 104 causes relative rotational motion between the polarizer in module 103 and the analyzer in module 105. Device 104 is well known in the art and is not described for this reason. The polarization of the reflected light is measured by the analyzer in module 105, and the signal processor 109 calculates the ellipsometric parameter values, tan(Ψ) and cos(Δ), from the polarization of the reflected light. The signal processor 109 uses the ellipsometric parameter values to derive polarization and phase information. The phase is Δ. The polarization angle α is related to tan(Ψ) through the following equation:

$$\tan\alpha = \frac{1}{\tan\Psi} \qquad (2)$$

The signal processor 109 determines misalignment from the polarization or phase information, as discussed above.

The imaging and focusing of the optical system 100 in one embodiment is verified using the vision and pattern recognition system 115. The light source 101 provides a beam for imaging and focusing 87. The beam for imaging and focusing 87 is reflected by beam splitter 113 and focused by lens 111 to the wafer 91. The beam 87 is then reflected back through the lens 111 and beam splitter 113 to the vision and pattern recognition system 115. The vision and pattern recognition system 115 then sends a recognition signal 88 for keeping the wafer in focus for measurement to the signal processor 109.

FIG. 10a illustrates an optical system 110 using normal incident radiation beam 82 and detecting first-order diffracted radiation 93, 95. A source 202 provides polarized incident radiation beam 82 to illuminate periodic structures on a wafer 91. In this embodiment, the source 202 comprises a light source 101, a polarizer 117 and lens 111. The structures diffract positive first-order diffracted radiation 95 and negative first-order diffracted radiation 93. Analyzers 121, 119 collect positive first-order diffracted radiation 95 and negative first-order diffracted radiation 93, respectively. Light detection units 125, 123 detect the positive first-order diffracted radiation 95 and the negative first-order diffracted radiation 93, respectively, collected by analyzers 121, 119, respectively, to provide output signals 85. A signal processor 109 determines any misalignment between the structures from the output signals 85, preferably by comparing the output signals 85 to a reference signal. In one embodiment, the signal processor 109 calculates a derived signal from the output signals 85. The derived signal is a differential signal between the positive first-order diffracted radiation 95 and the negative first-order diffracted radiation 93. The differential signal can indicate a differential intensity, a differential polarization angle, or a differential phase.

Optical system 110 determines differential intensity, differential polarization angles, or differential phase. To determine differential phase, optical system 110 in one embodiment uses an ellipsometric arrangement comprising a light source 101, a polarizer 117, an analyzer 119 or 121, a light detector 123 or 125, and a device 104 that causes relative rotational motion between the polarizer 117 and the analyzer 119 or 121. Device 104 is well known in the art and is not described for this reason. This arrangement provides ellipsometric parameters for positive first-order diffracted radiation 95 and ellipsometric parameters for negative first-order diffracted radiation 93, which are used to derive phase for positive first-order diffracted radiation 95 and phase for negative first-order diffracted radiation 93, respectively. As discussed above, one of the ellipsometric parameters is cos(Δ), and the phase is Δ. Differential phase is calculated by subtracting the phase for the negative first-order diffracted radiation 93 from the phase for the positive first-order diffracted radiation 95.

To determine differential polarization angles, in one embodiment, the polarizer 117 is fixed for the incident radiation beam 82, and the analyzers 121, 119 are rotated, or vice versa. The polarization angle for the negative first-order diffracted radiation 93 is determined from the change in intensity as either the polarizer 117 or analyzer 119 rotates. The polarization angle for the positive first-order diffracted radiation 95 is determined from the change in intensity as either the polarizer 117 or analyzer 121 rotates. A differential polarization angle is calculated by subtracting the polarization angle for the negative first-order diffracted radiation 93 from the polarization angle for the positive first-order diffracted radiation 95.

To determine differential intensity, in one embodiment, the analyzers 119, 121 are positioned without relative rotation at the polarization angle of the first-order diffracted radiation 93, 95. Preferably, at the polarization angle where the intensity of the diffracted radiation is a maximum, the intensity of the positive first-order diffracted radiation 95 and the intensity of the negative first-order diffracted intensity 93 is detected by the detectors 125, 123. Differential intensity is calculated by subtracting the intensity for the negative first-order diffracted radiation 93 from the intensity for the positive first-order diffracted radiation 95.

In another embodiment, the differential intensity is measured as a function of the incident polarization angle. In this embodiment, the polarizer 117 is rotated, and the analyzers 119, 121 are fixed. As the polarizer 117 rotates, the incident polarization angle changes. The intensity of the positive first-order diffracted radiation 95 and the intensity of the negative first-order diffracted radiation 93 is determined for different incident polarization angles. Differential intensity is calculated by subtracting the intensity for the negative first-order diffracted radiation 93 from the intensity for the positive first-order diffracted radiation 95.

The imaging and focusing of the optical system 110 in one embodiment is verified using the vision and pattern recognition system 115. After incident radiation beam 82 illuminates the wafer 91, a light beam for imaging and focusing 87 is reflected through the lens 111, polarizer 117, and beam splitter 113 to the vision and pattern recognition system 115. The vision and pattern recognition system 115 then sends a recognition signal 88 for keeping the wafer in focus for measurement to the signal processor 109.

FIG. 11a illustrates an optical system 120 where first-order diffracted radiation beams 93, 95 are allowed to interfere. The light source 101, device 104, polarizer 117, lens 111, and analyzers 119, 121 operate the same way in optical system 120 as they do in optical system 110. Device 104 is well known in the art and is not described for this reason. Once the negative first-order diffracted radiation 93 and positive first-order diffracted radiation 95 are passed through the analyzers 119, 112, respectively, a first device causes the positive first-order diffracted radiation 95 and the negative first-order diffracted radiation 93 to interfere. In this embodiment, the first device comprises a multi-aperture shutter 131 and a flat beam splitter 135. The multi-aperture shutter 131 allows both the negative first-order diffracted radiation 93 and the positive first-order diffracted beam 95 to pass through it. The flat beam splitter 135 combines the negative first-order diffracted radiation 93 and the positive first-order diffracted radiation 95. In this embodiment, the mirrors 127, 133 change the direction of the positive first-order diffracted radiation 95. A light detection unit 107 detects the interference 89 of the two diffracted radiation signals to provide output signals 85. A signal processor 109 determines any misalignment between the structures from the output signals 85, preferably by comparing the output signals 85 to a reference signal. The output signals 85 contain information related to phase difference.

In one embodiment, phase shift interferometry is used to determine misalignment. The phase modulator 129 shifts the phase of positive first-order diffracted radiation 95. This phase shift of the positive first-order diffracted radiation 95 allows the signal processor 109 to use a simple algorithm to calculate the phase difference between the phase for the positive first-order diffracted radiation 95 and the phase for the negative first-order diffracted radiation 93.

Differential intensity and differential polarization angle can also be determined using optical system 120. The multi-aperture shutter 131 operates in three modes. The first mode allows both the positive first-order diffracted radiation 95 and the negative first-order diffracted radiation 93 to pass through. In this mode, differential phase is determined, as discussed above. The second mode allows only the positive first-order diffracted radiation 95 to pass through. In this mode, the intensity and polarization angle for the positive first-order diffracted radiation 95 can be determined, as discussed above. The third mode allows only the negative first-order diffracted radiation 93 to pass through. In this mode, the intensity and polarization angle for the negative first-order diffracted radiation 93 can be determined, as discussed above.

To determine differential intensity, the multi-aperture shutter 131 is operated in the second mode to determine intensity for positive first-order diffracted radiation 95 and then in the third mode to determine intensity for negative first-order diffracted radiation 93, or vice versa. The differential intensity is then calculated by subtracting the intensity of the negative first-order diffracted radiation 93 from the intensity of the positive first-order diffracted radiation 95. The signal processor 109 determines misalignment from the differential intensity.

In one embodiment, the differential intensity is measured at different incident polarization angles. The measurements result in a large set of data points, which, when compared to a reference signal, provide a high accuracy in the determined value of the misregistration.

To determine differential polarization angle, the multi-aperture shutter 131 is operated in the second mode to determine polarization angle for positive first-order diffracted radiation 95 and then in the third mode to determine polarization angle for negative first-order diffracted radiation 93, or vice versa. The differential polarization angle is then calculated by subtracting the polarization angle of the negative first-order diffracted radiation 93 from the polarization angle of the positive first-order diffracted radiation 95. The signal processor 109 determines misalignment from the differential polarization angle.

The imaging and focusing of the optical system 120 is verified using the vision and pattern recognition system 115 in the same way as the imaging and focusing of the optical system 110 is in FIG. 10. In one embodiment, the beam splitter 113 splits off radiation 89 to reference light detection unit 137, which detects fluctuations of the light source 101. The reference light detection unit 137 communicates information 86 concerning intensity fluctuation of source 101 to the signal processing and computing unit 109. The signal processor 109 normalizes the output signal 85 using fluctuation information 86.

Figure 9B:
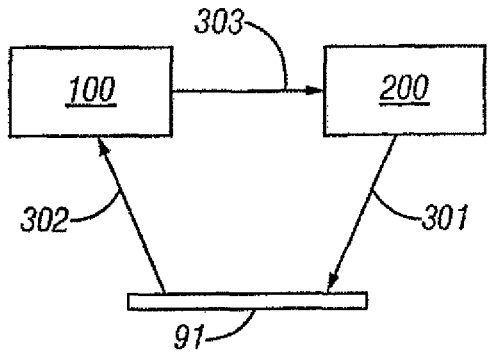
FIG. 9b is a schematic block diagram of an integrated system of the optical system of FIG. 9a and a deposition instrument.
Figure 10B:
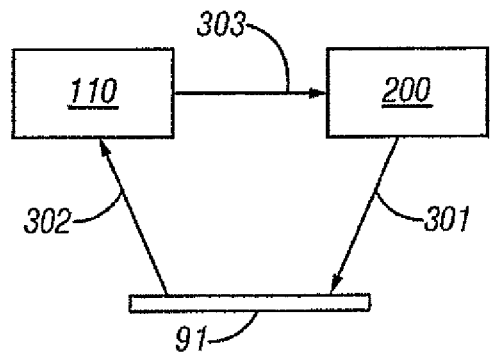
FIGS. 10b and 11b are schematic block diagrams of integrated systems of the optical systems of FIGS. 10a and 11a, respectively, and a deposition instrument.
Figure 11B:
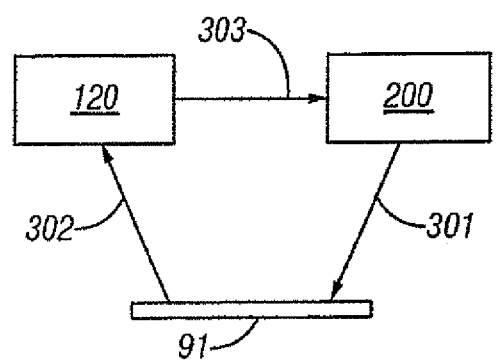

Optical systems 100, 110, 120 can be integrated with a deposition instrument 200 to provide an integrated tool, as shown in FIGS. 9b, 10b and 11b. The deposition instrument 200 provides the overlying or interlaced periodic structures on wafer 91 in step 301. Optical systems 100, 110, 120 obtains misalignment information from the wafer 91 in step 302. The signal processor 109 of optical systems 100, 110, 120 provides the misalignment to the deposition tool 200 in step 303. The deposition tool uses the misalignment information to correct for any misalignment before providing another layer or periodic structure on wafer 91 in step 301.

Optical systems 100, 110, 120 are used to determine the misalignment of overlying or interlaced periodic structures. The source providing polarized incident radiation beam illuminates the first periodic structure 13 and the second periodic structure 15. Diffracted radiation from the illuminated portions of the overlying or interlaced periodic structures are detected to provide an output signal 85. The misalignment between the structures is determined from the output signal 85. In a preferred embodiment, the misalignment is determined by comparing the output signal 85 with a reference signal, such as a reference signal from a calibration wafer or a database, compiled as explained below.

The invention relates to a method for providing a database to determine misalignment of overlying or interlaced periodic structures. The misalignment of overlying or interlaced periodic structures and structure parameters, such as thickness, refractive index, extinction coefficient, or critical dimension, are provided to calculate data related to radiation diffracted by the structures in response to a beam of radiation. The data can include intensity, polarization angle, or phase information. Calculations can be performed using known equations or by a software package, such as Lambda SW, available from Lambda, University of Arizona, Tucson, Ariz., or Gsolver SW, available from Grating Solver Development Company, P.O. Box 353, Allen, Tex. 75013. Lambda SW uses eigenfunctions approach, described in P. Sheng, R. S. Stepleman, and P. N. Sandra, Exact Eigenfunctions for Square Wave Gratings: Applications to Diffraction and Surface Plasmon Calculations, Phys. Rev. B, 2907-2916 (1982), or the modal approach, described in L. Li, A Modal Analysis of Lamellar Diffraction Gratings in Conical Mountings, J. Mod. Opt. 40, 553-573 (1993). Gsolver SW uses rigorous coupled wave analysis, described in M. G. Moharam and T. K. Gaylord, Rigorous Coupled-Wave Analysis of Planar-Grating Diffraction, J. Opt. Soc. Am. 73, 1105-1112 (1983). The data is used to construct a database correlating the misalignment and the data. The overlay misregistration of a target can then be determined by comparing the output signal 85 with the database.

Figure 12A:
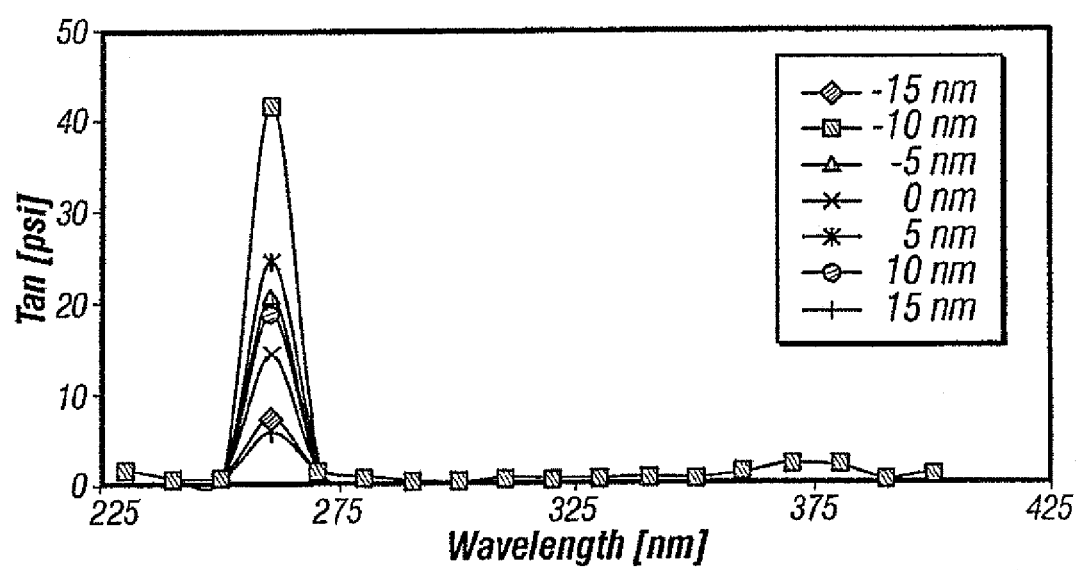
FIGS. 12a and 12b are graphical plots of derived signals from zero-order diffraction of incident radiation on overlying structures.
Figure 12B:
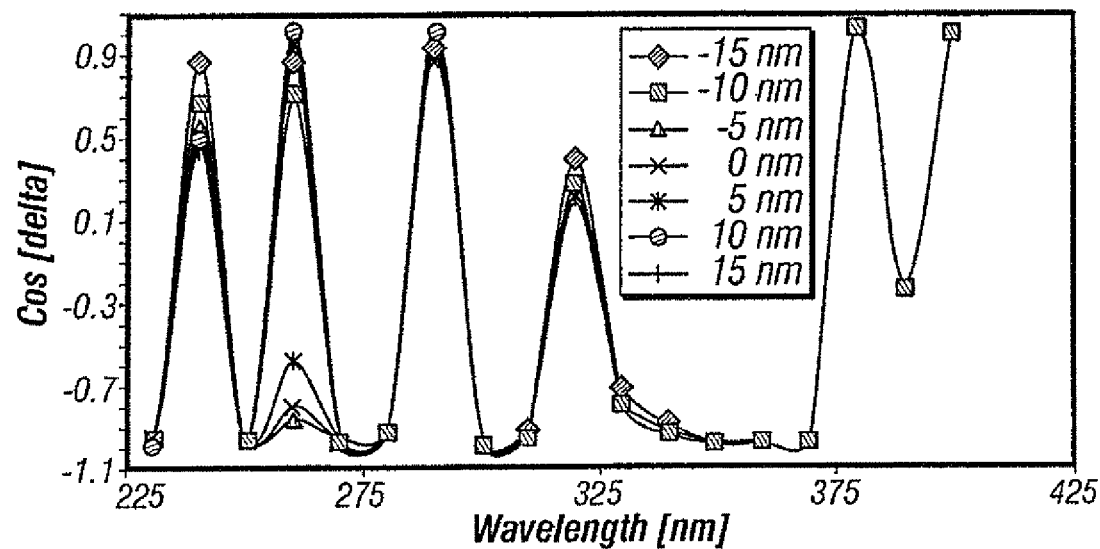

FIGS. 12-24 were generated through computer simulations using either the Lambda SW or the Gsolver SW. FIGS. 12a and 12b are graphical plots illustrating the ellipsometric parameters obtained using an overlying target of FIG. 2a with the optical system of FIG. 9a. The calculations were performed using the Lambda SW. The overlying target used in the measurement comprises first periodic structure 13 and the second periodic structure 15 made of resist gratings having 1 μm depth on a silicon substrate. The depth of the first periodic structure 13 and the second periodic structure 15 is 0.5 μm, and the pitch is 0.8 μm. The first selected width CD1 for the first periodic structure 13 is 0.4 μm, and the second selected width CD2 for the second periodic structure 15 is 0.2 μm. The incident beam in this embodiment was TE polarized. These target parameters and the overlay misregistration were inputted into the Lambda SW to obtain ellipsometric parameter values. The ellipsometric parameter values were obtained for zero-order diffracted radiation using an incident radiation beam 81 at an angle of 25° to the wafer surface. The ellipsometric parameters, Tan [Ψ] and Cos [Δ], were plotted as a function of the wavelengths in the spectral range 230 to 400 nanometers. The ellipsometric parameters are defined as:

$$\tan \Psi = \frac{|r_p|}{|r_s|} \tag{3}$$

where $r_p$ and $r_s$ are the amplitude reflection coefficients for the p(TM) and s(TE) polarizations, and $$\Delta = \phi_p - \phi_s \tag{4}$$

where $\phi_p$ and $\phi_s$ are the phases for the p(TM) and s(TE) polarizations. Results were obtained for different values of overlay misregistration $d_2 - d_1$ varying from −15 nanometers to 15 nanometers in steps of 5 nanometers. The variations for tan [Ψ] and cos [Δ] show sensitivity to the misregistration in the nanometer scale. To get more accurate results, first-order diffracted radiation is detected using normal incident radiation, as in FIGS. 13-14.

Figure 13:
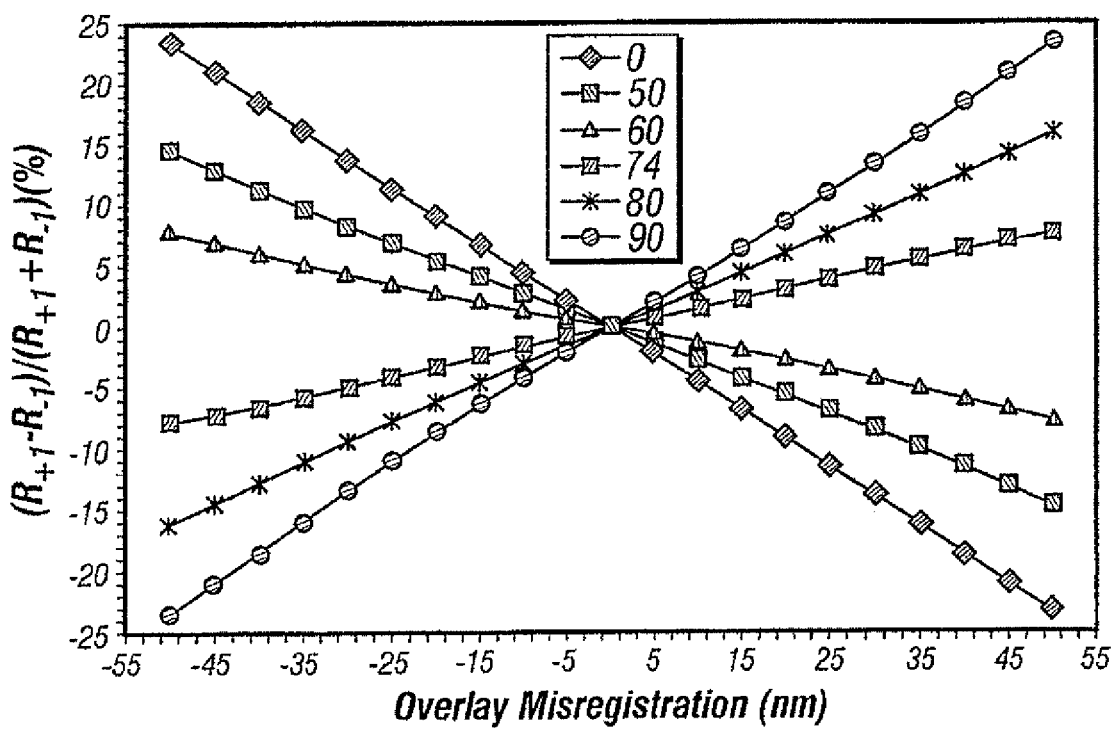
FIGS. 13-14 and 16-17 are graphical plots of derived signals from first-order diffraction of incident radiation on overlying structures.
Figure 14:
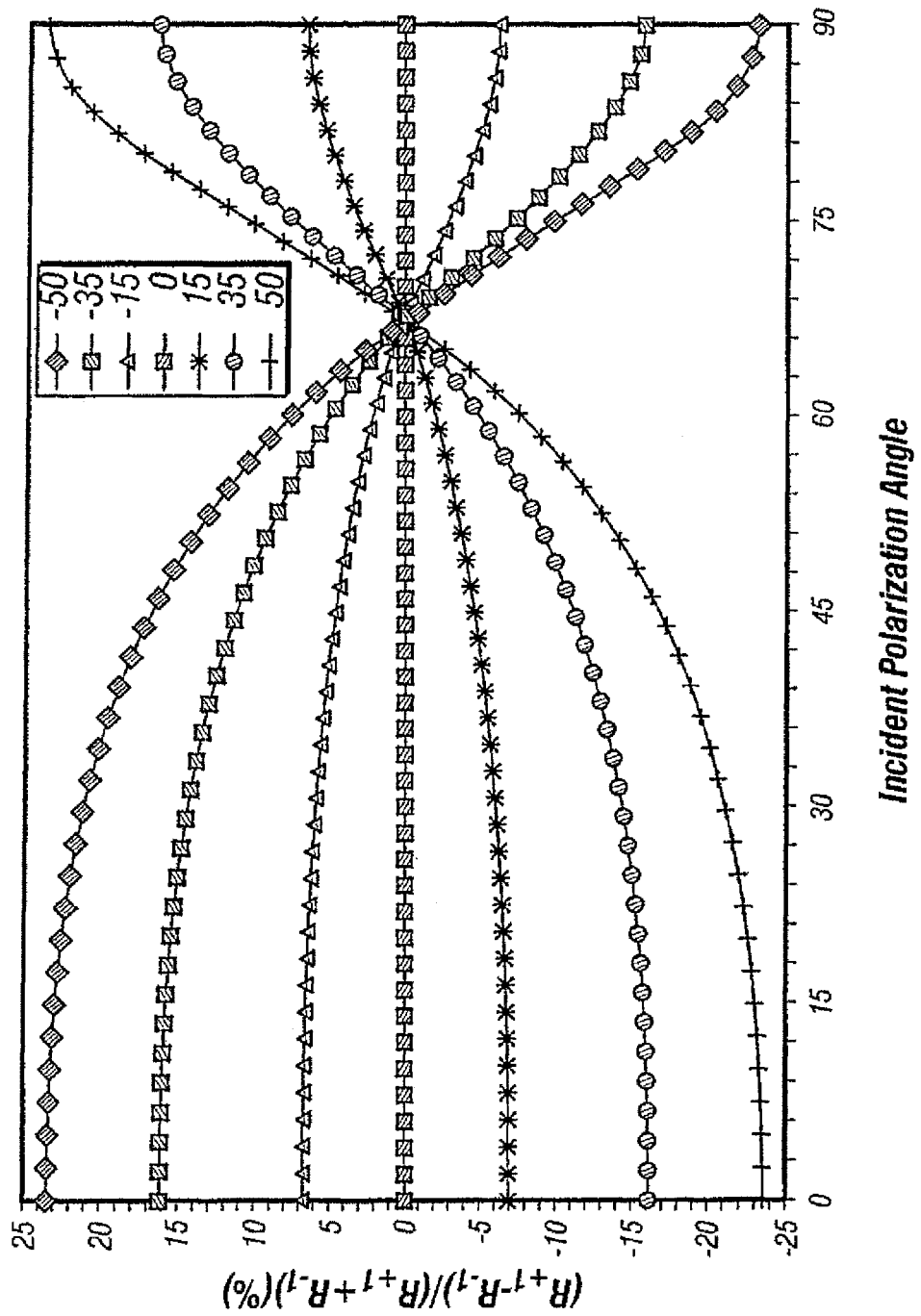
Figure 15:
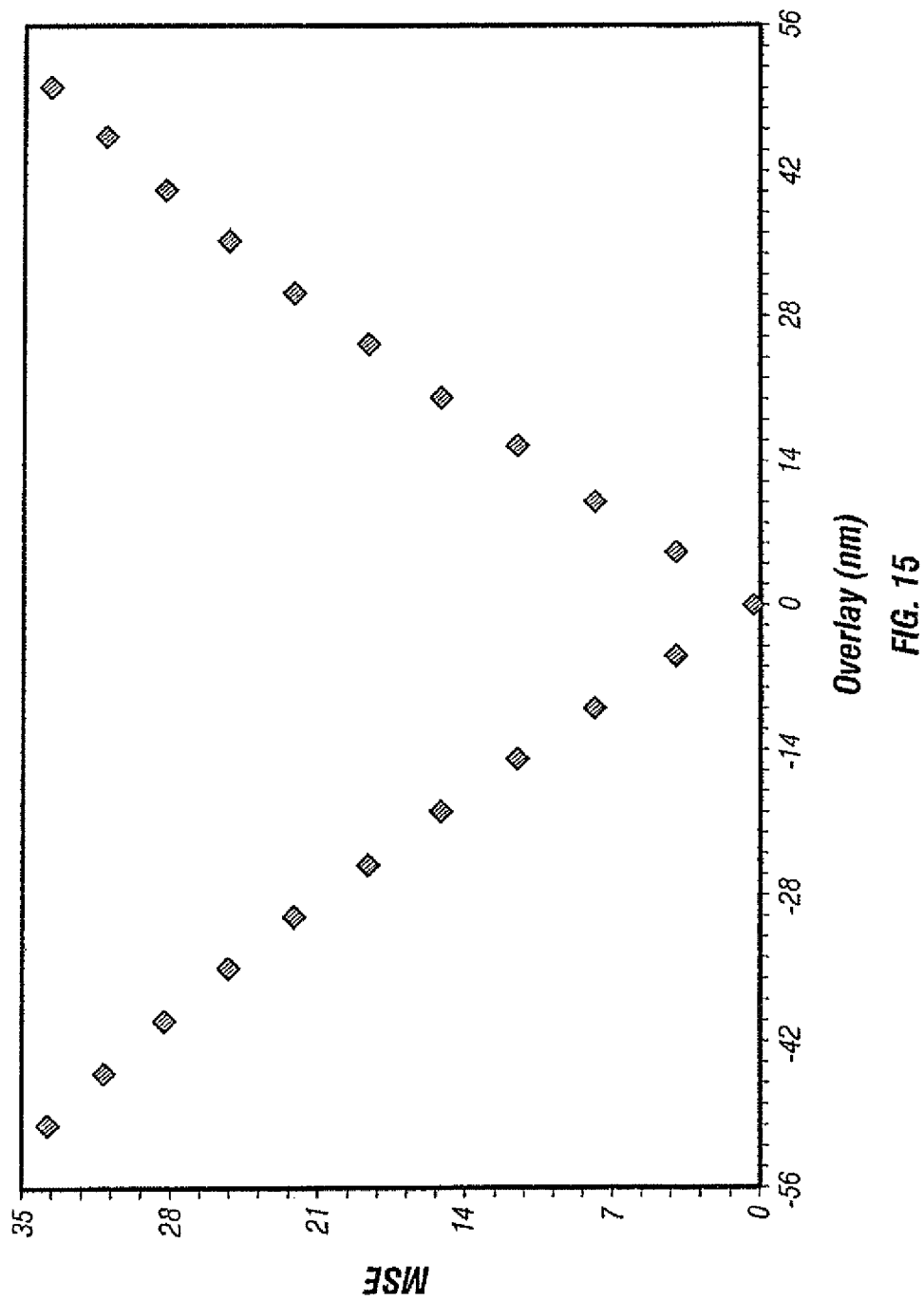
FIG. 15 is a graphical plot illustrating the mean square error.

FIGS. 13 and 14 are graphical plots illustrating the differential intensity obtained using overlying targets of FIG. 2a and an optical system detecting first-order diffracted radiation using normal incident radiation. The calculations were performed using Gsolver SW. The first periodic layer 13 is etched silicon, while the second periodic layer 15 is resist. The overlay misregistration and target parameters were inputted into Gsolver SW to obtain the differential intensity in FIGS. 13 and 14. FIG. 13 shows the normalized differential intensity between the positive and negative first-order diffracted radiation as a function of overlay misregistrations. The differential intensity is defined as:

$$DS = \frac{R_{+1} - R_{-1}}{R_{+1} + R_{-1}} \% \tag{5}$$

where $R_{+1}$ is the intensity of the positive first-order diffracted radiation and $R_{-1}$ is the intensity of the negative first-order diffracted radiation. The different curves in FIG. 13 correspond to the different incident polarization angles (0°, 50°, 60°, 74°, 80°, and 90°) of the incident linearly polarized light relative to the plane of incidence. The polarization angle α is defined as:

$$\alpha = \arctan\left(\frac{|E_s|}{|E_p|}\right) \tag{6}$$

where $E_s$ is the field component perpendicular to the plane of incidence, which for normal incidence is the Y component in the XY coordinate system, and $E_p$ is the field component parallel to the plane of incidence, which for normal incidence is the X component. Polarization scans from incident polarization angles of 0° to 90° were performed to generate the graphical plots in FIGS. 13 and 14. FIG. 14 shows the differential intensity as a function of incident polarization angle at different overlay misregistration (−50 nm, −35 nm, −15 nm, 0 nm, 15 nm, 35 nm, and 50 nm). FIG. 14 shows that there is a neutral polarization angle, defined as an incident polarization angle where the differential intensity is equal to zero for all overlay misregistration. FIGS. 13 and 14 illustrate the high sensitivity of differential intensity to the overlay misregistration and the linear behavior of differential intensity with the overlay misregistration. They also show that the differential intensity is zero at zero overlay misregistration for any polarization angle. Similar graphical plots were obtained at different wavelengths. FIG. 15 shows the mean square error ("MSE") variation with the overlay misregistration. The MSE exhibits linearity and sensitivity of approximately 0.6 per one nanometer overlay misregistration.

Figure 16:
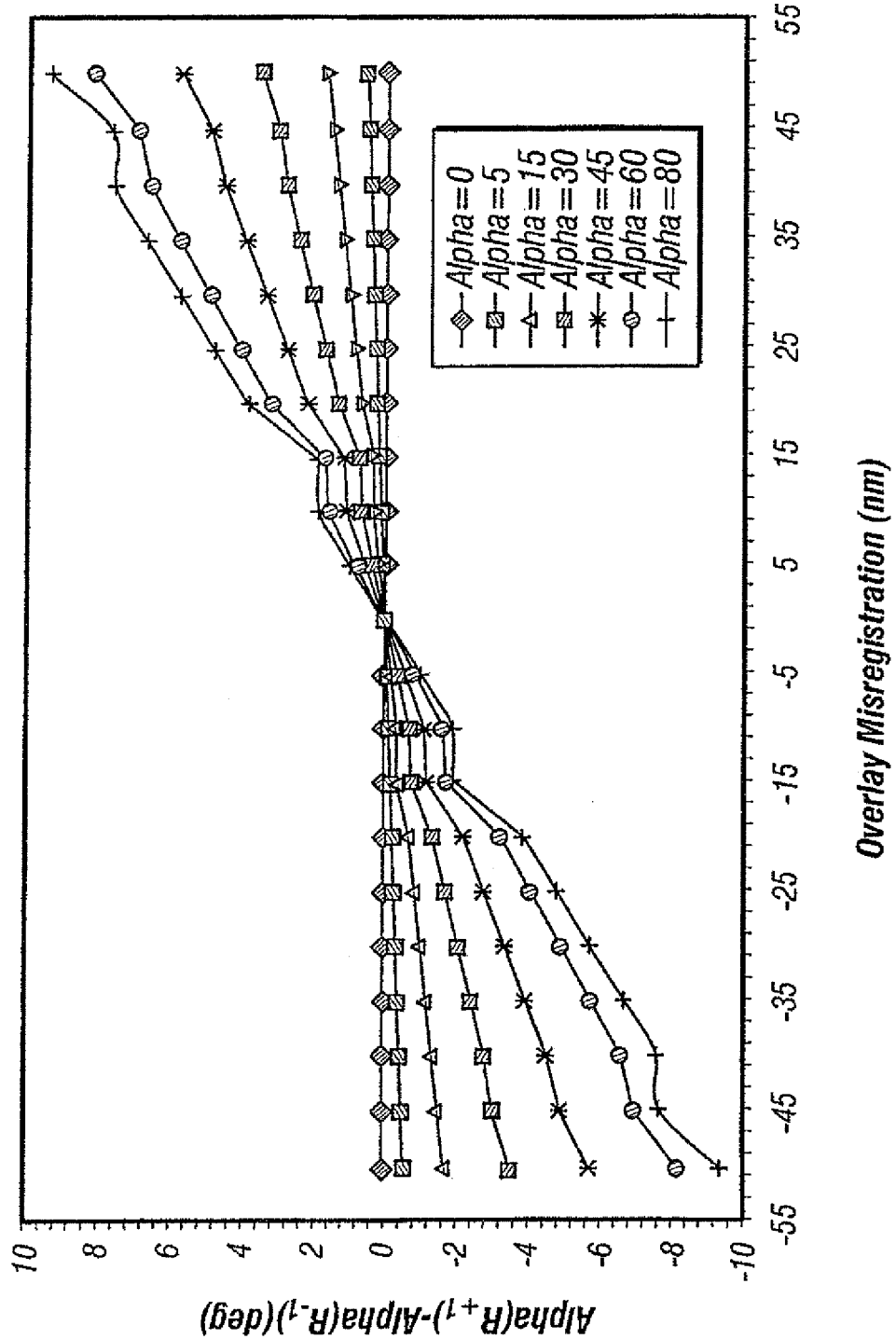
Figure 17:
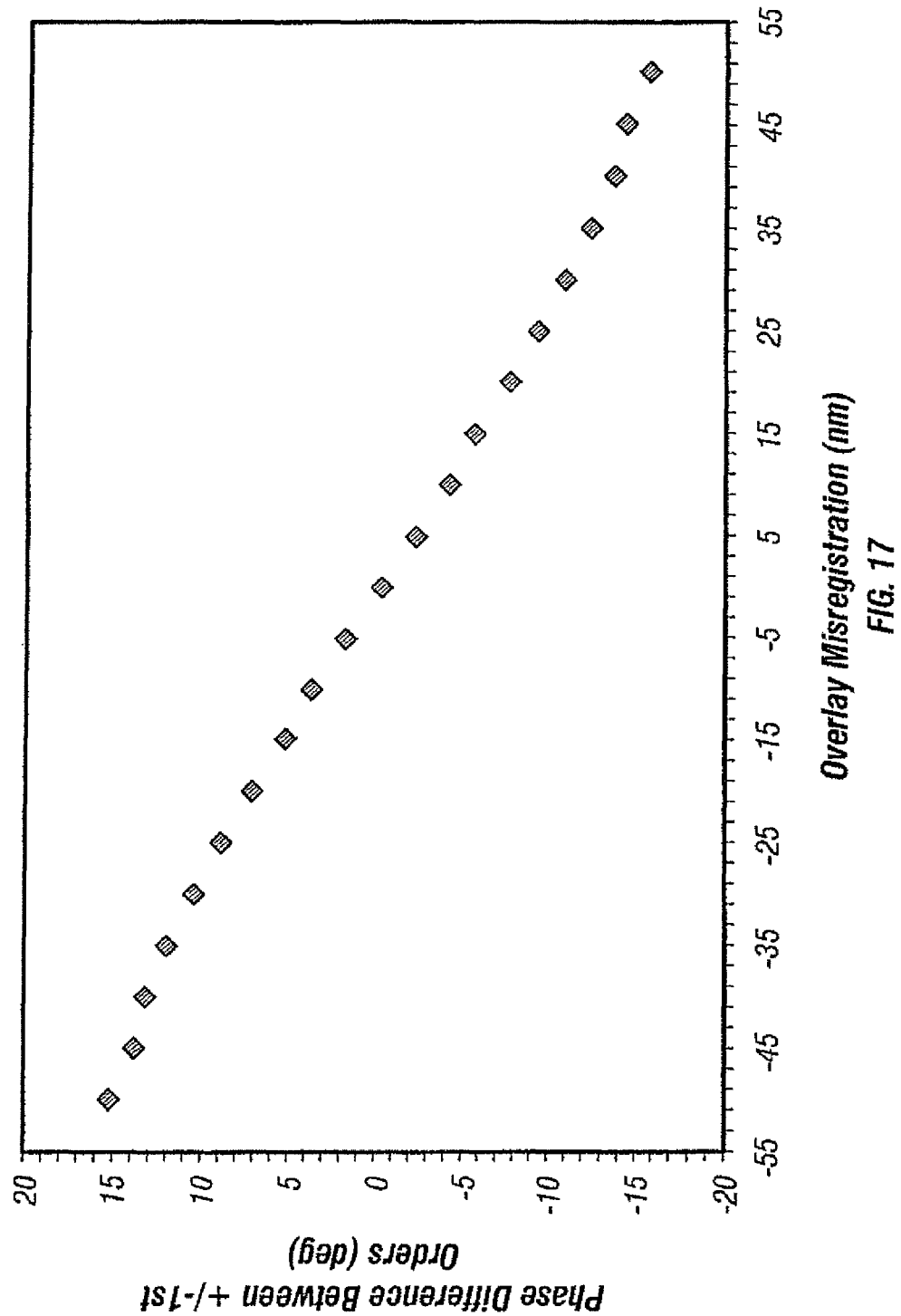

FIGS. 16 and 17 are graphical plots, using the same target with different structure parameters and the same optical system as the ones in FIGS. 13 and 14. However, the calculations were performed using the Lambda SW, instead of the Gsolver SW. The kinks or the deviations from the montonicity of the curves at certain points in FIGS. 16 and 17 are believed to be due to numerical instabilities frequently known to occur in the use of the Lambda SW. The overlay misregistration and the target parameters were inputted into Lambda SW to obtain differential polarization angle and differential phase in FIGS. 16 and 17, respectively. FIG. 16 shows the variation of the difference between the polarization angles of the positive and negative first-order diffracted radiation as a function of overlay misregistration for different incident polarization angles (0°, 5°, 15°, 30°, 45°, 60°, and 90°). FIG. 17 shows the variation of the difference between the phase angles of the positive and negative first-order diffracted radiation. The phase angle here represents the phase difference between the p and s polarized components of the diffracted light.

FIGS. 16 and 17 also illustrate the high sensitivity of differential polarization angle and differential phase, respectively, to the overlay misregistration and the linear behavior of differential polarization angle and differential phase, respectively, when plotted against the overlay misregistration. They also show that the differential polarization angle and differential phase is zero at zero overlay misregistration for any polarization angle. However, FIG. 17 shows that the phase difference does not depend on incident polarization. In one embodiment, the difference between the polarization angles, as shown in FIG. 16, is easily measured with an analyzer at the output, while the phase difference, as shown in FIG. 17, is measured with interferometry. In another embodiment, the differential polarization angle and the differential phase is derived from ellipsometric parameters.

Similar results were obtained using the overlying targets in FIGS. 4a and 4b. However, for the particular target in FIG. 4a, there was no neutral polarization angle in the line on line configuration, where the second periodic structure 15 is centered on the first periodic structure 13. The line on space configuration, where the second periodic structure 15 is centered on the spaces between the first periodic structure 13, did exhibit a neutral polarization angle. These results show that the neutral polarization angle apparently has a complicated dependence on the structure parameters.

FIGS. 18-19 and 21-22 are graphical plots illustrating the intensity of the zero-order diffracted radiation 83, as shown in FIG. 9a, for interlaced gratings, as shown in FIG. 6. Table 1 summarizes the parameters used in the calculations by the Gsolver SW.

TABLE 1

Structure parameters used in the simulations

| Parameter | Data76 | Data0 |
| --- | --- | --- |
| h1 | 850 nm | 850 nm |
| h2 | 850 nm | 850 nm |
| h3 | 600 nm | 600 nm |
| Pitch (P) | 1000 nm | 2000 nm |
| CD1 | 150 nm | 200 nm |
| CD2 | 300 nm | 600 nm |
| CD3 | 150 nm | 200 nm |
| Incidence angle (θ) | 76° | 0 |
| Azimuth angle (φ) | 0 | 0 |
| Wavelength (λ) | 670 nm | 500 nm |

The incidence angle is 76° in the Data76 configuration, and the incidence angle is 0° (normal) in the Data0 configuration.

Figure 18:
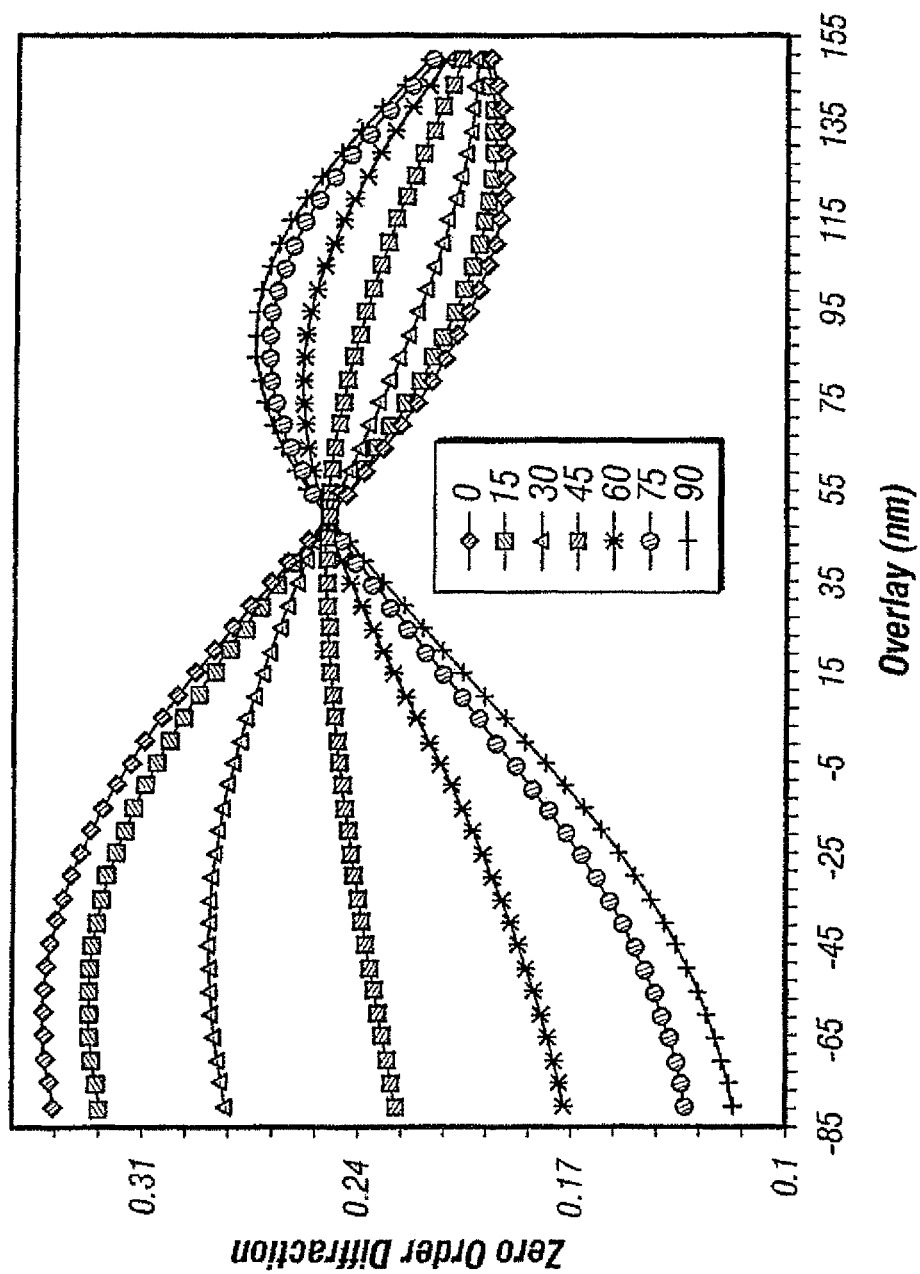
FIGS. 18-19 and 21-22 are graphical plots of derived signals from zero-order diffraction of incident radiation on interlaced gratings.
Figure 19:
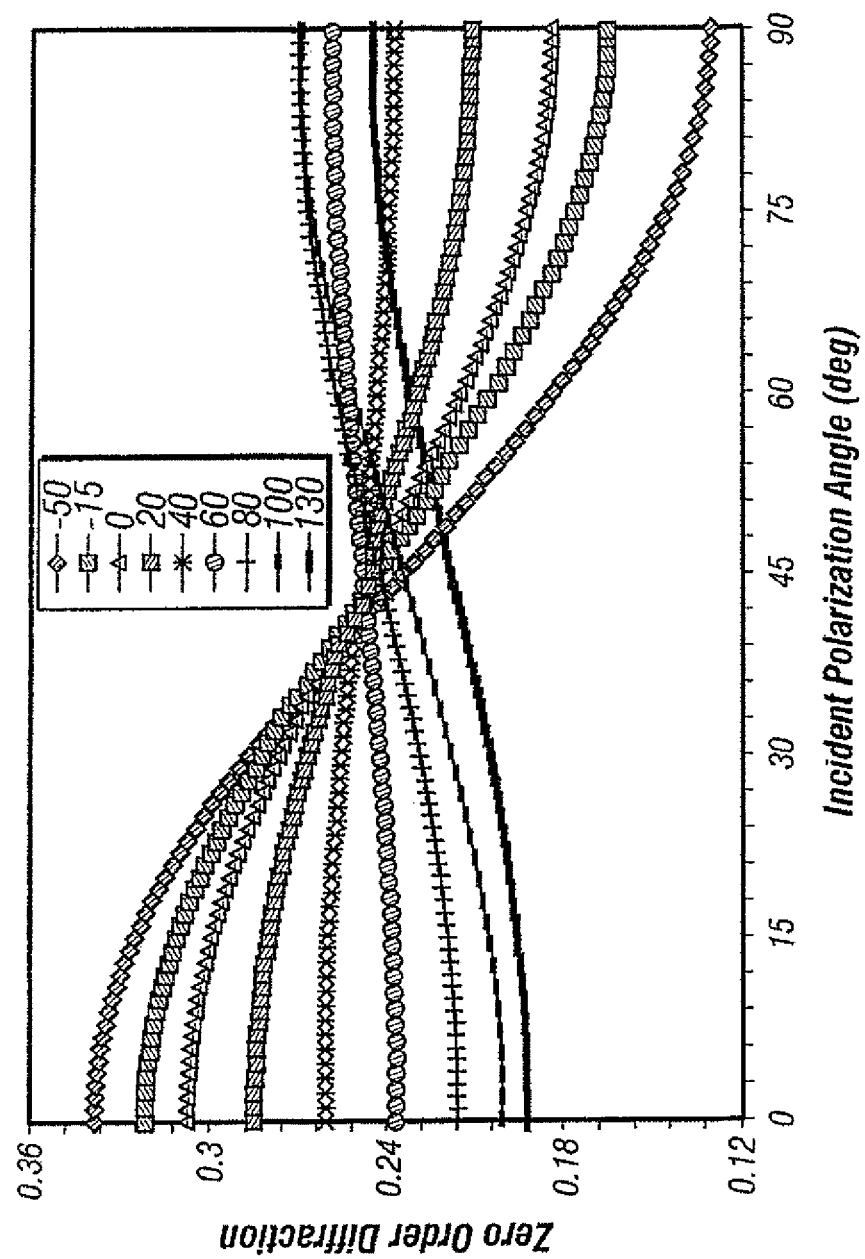
Figure 20:
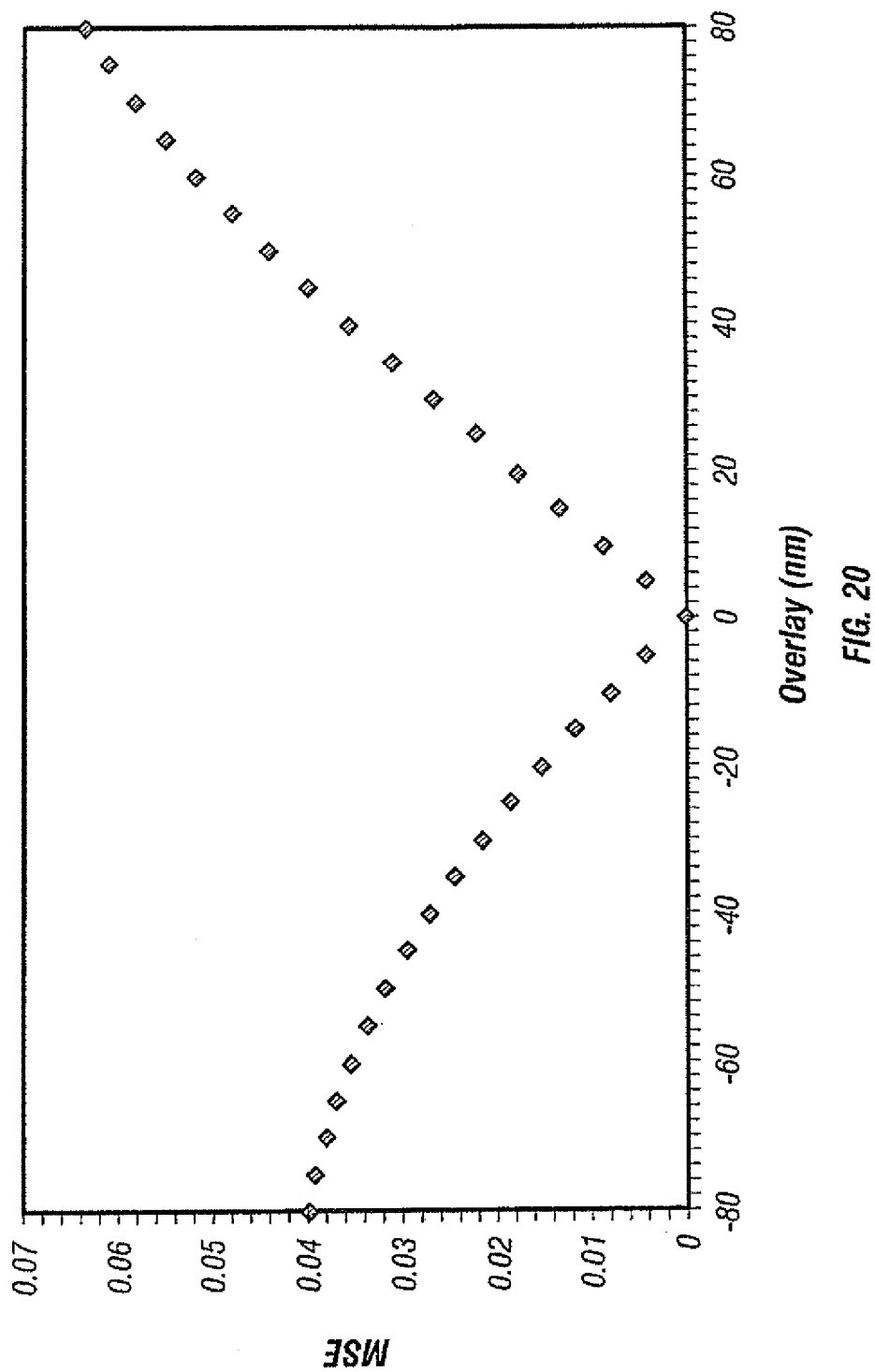
FIGS. 20 and 23 are graphical plots illustrating the mean square error.

FIGS. 18-20 were derived using the Data76 configuration. FIG. 18 shows the intensity of the zero-order diffracted radiation versus the overlay misregistration at different polarization angles (0° to 90° in steps of 15°). Within a range of 140 nm, the changes are monotonic with the overlay misregistration. The point where all the curves cross is at an overlay misregistration value of 50 nm, rather than zero. At an overlay misregistration value of 50 nm, the structure is effectively most symmetric. In contrast, in an overlying target as in FIG. 2a, the structure is most symmetric at zero overlay misregistration. FIG. 19 shows the dependence of the intensity of the zero-order diffracted radiation on the incident polarization angle at different overlay misregistrations (−50 nm, −15 nm, 0 nm, 20 nm, 40 nm, 60 nm, 80 nm, 100 nm, and 130 nm). Unlike with the differential intensity of the first-order diffracted radiation, there is not a neutral polarization angle where the differential intensity is zero for different overlay misregistration. However, there is a quasi-neutral polarization angle where most of the curves for different misregistration cross. FIG. 20 shows the MSE variation as a function of overlay misregistration. FIGS. 18 and 19 show the high sensitivity of the intensity of zero-order diffracted radiation to the overlay sign for a configuration using incident radiation having an oblique angle of incidence on interlaced gratings. They also show the linear behavior of the intensity when plotted against the overlay misregistration.

Figure 21:
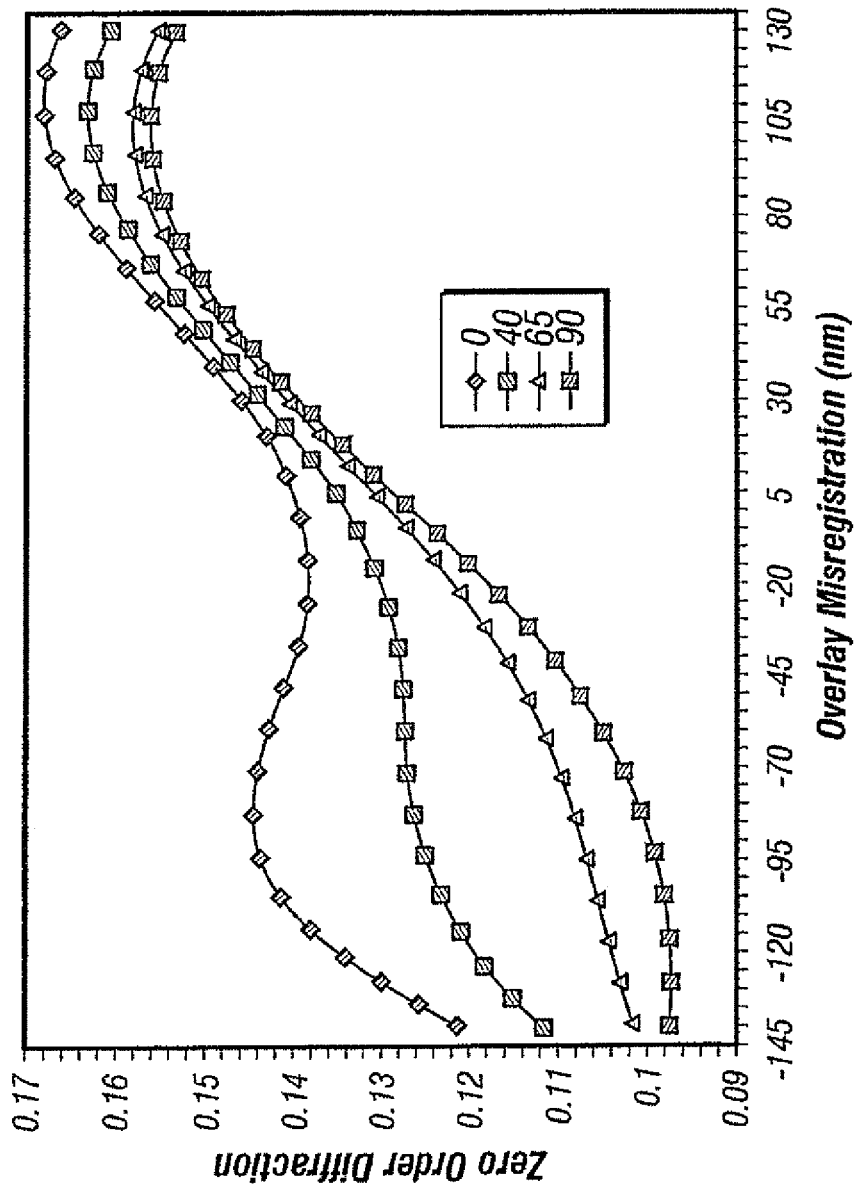
Figure 22:
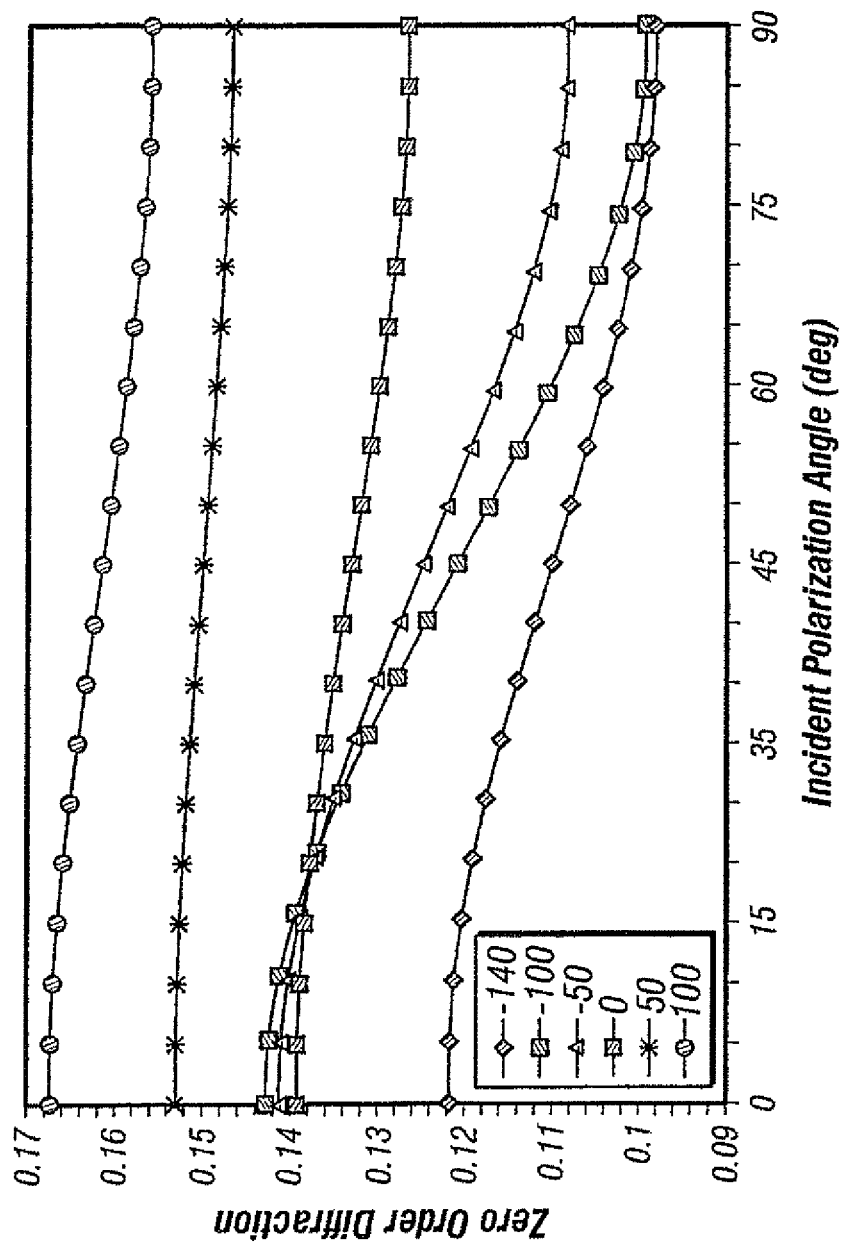
Figure 23:
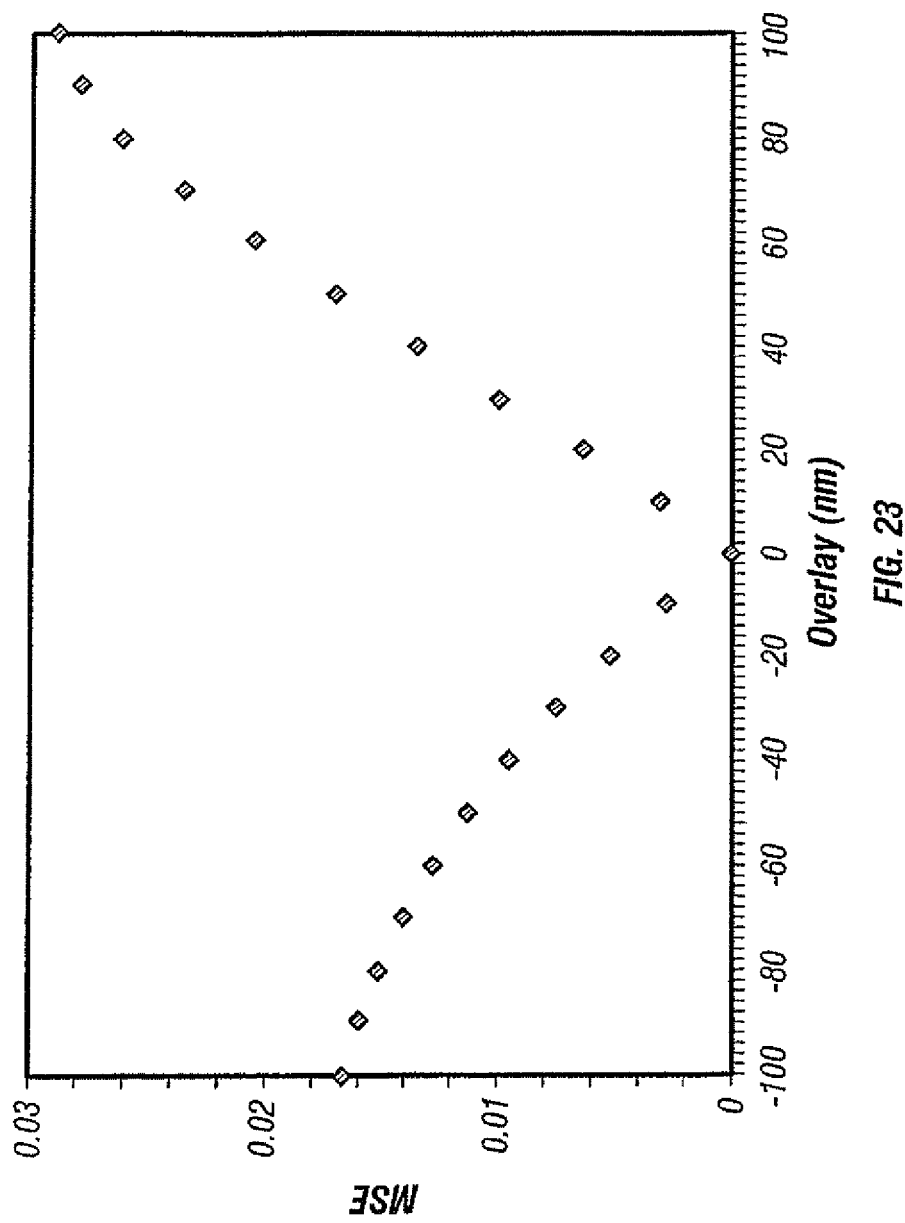

FIGS. 21-23 were derived using the Data0 configuration. FIG. 21 shows the intensity of the zero-order diffracted radiation versus the overlay misregistration at different polarization angles (0°, 40°, 65°, and 90°). FIG. 22 shows the dependence of the intensity of the zero-order diffracted radiation on the incident polarization angle at different overlay misregistrations (−140 nm, −100 nm, −50 nm, 0 nm, 50 nm, and 100 nm). FIG. 23 shows the MSE variation as a function of overlay misregistration. FIGS. 21 and 22 show the high sensitivity of the intensity of zero-order diffracted radiation to the overlay sign for a configuration using normal incident radiation on interlaced gratings. They also show the linear behavior of the intensity when plotted against the overlay misregistration.

Figure 24:
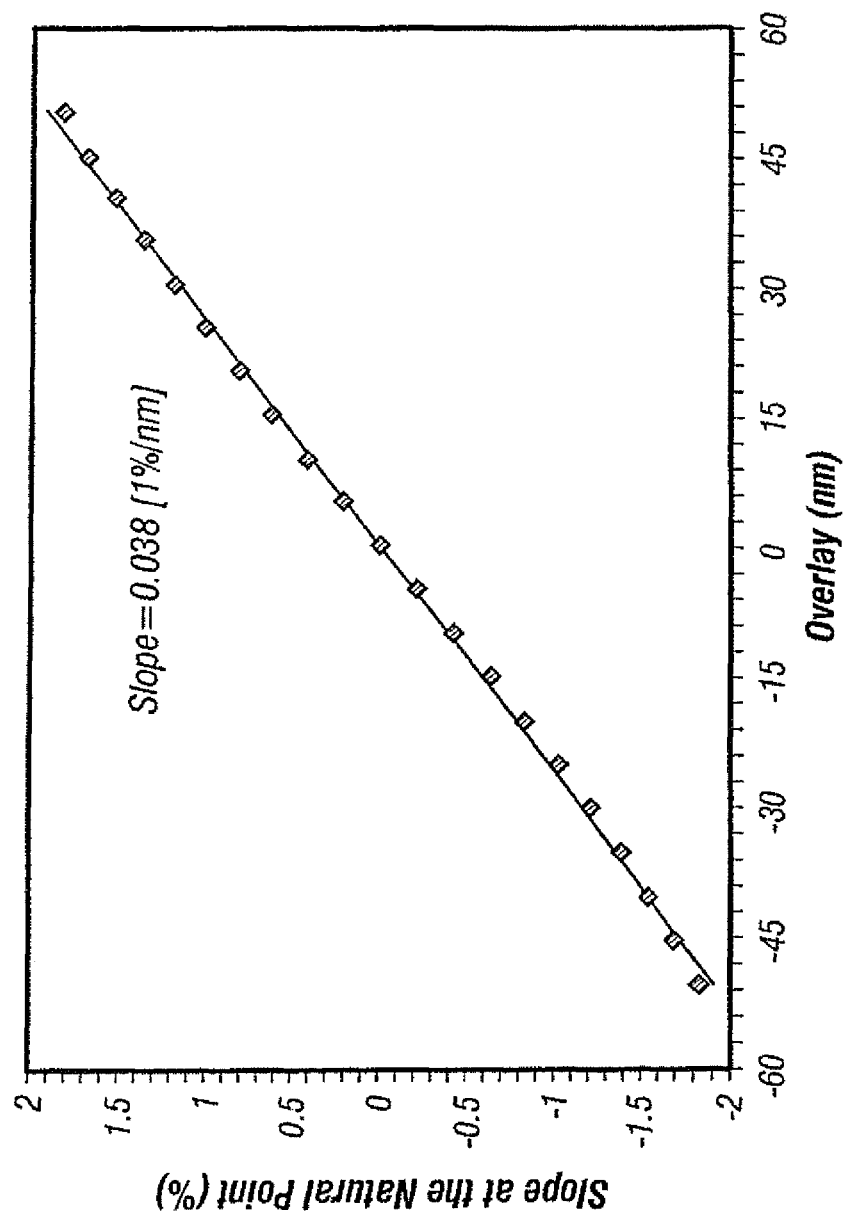
FIG. 24 is a graphical plot illustrating the determination of misalignment from a slope near a neutral polarization angle.

FIG. 24 is a graphical plot generated by the Gsolver SW illustrating the determination of misalignment from the neutral polarization angle. As shown in FIG. 14, the differential intensity equals zero independent of the overlay misregistration at the neutral polarization angle. However, the slope of the differential intensity varies with overlay misregistration. FIG. 24 shows the slope near the neutral polarization angle as a function of overlay misregistration. FIG. 24 shows linear behavior of the slope versus the overlay misregistration with a slope of 0.038% per 1 nm overlay misregistration. An advantage of the slope measurement technique is the reduction of the number of parameters that need to be determined. Another advantage is the decreased polarization scanning needed. In FIG. 14, a polarization scan using incident polarization angles from 0° to 90° is performed. In contrast, using the slope measurement technique in one embodiment, the derived signal is compared with the reference signal for polarization angles within about five degrees of the neutral polarization angle. Thus, the method of detecting misalignment is faster when using the slope measurement technique. Another embodiment of the invention is the use of the slope measurement technique for the quasi-neutral polarization angle.

Misalignment of overlying or interlaced periodic structures can be determined using the database in a preferred embodiment. The source providing polarized incident radiation illuminates the first periodic structure 13 and the second periodic structure 15. Diffracted radiation from the illuminated portions of the overlying or interlaced periodic structures are detected to provide an output signal 85. The output signal 85 is compared with the database to determine the misalignment between the overlying or interlaced periodic structures.

In another embodiment, misalignment of overlying or interlaced periodic structures is determined using the slope measurement technique. A neutral polarization angle or quasi-neutral polarization angle is provided. The derived signal is compared with the reference signal near the neutral polarization angle or the quasi-neutral polarization angle to determine misalignment of the overlying or interlaced periodic structures.

While the invention has been described above by reference to various embodiments, it will be understood that changes and modifications may be made without departing from the scope of the invention, which is to be defined only by the appended claims and their equivalent. All references referred to herein are incorporated by reference.

What is claimed is:

1. A method for processing and measuring a device, said device having a first periodic structure, said method comprising:
    measuring the first periodic structure by illuminating the first periodic structure with incident radiation and by detecting diffracted radiation from the illuminated portions of the first periodic structure;
    after the first periodic structure has been measured, forming a second periodic structure in a region of the device, where the first and second periodic structures are present in said region and said second periodic structure includes a first and a second portion, wherein the first portion is in the region where the first periodic structure is present and the second portion is in a second region where the first periodic structure is not present;
    measuring a relative position between the first and second periodic structures by illuminating the first and second periodic structures with incident radiation and by detecting diffracted radiation from the illuminated portions of the first and second periodic structures in said region; and
    measuring the second periodic structure by measuring said second portion of said second periodic structure in the second region.

2. The method of claim 1, wherein the second periodic structure is formed so that the first and second periodic structures overlie one another in the region.

3. The method of claim 1, wherein a critical dimension of the first periodic structure is measured.

4. The method of claim 1, wherein a width of the first periodic structure is measured.

5. The method of claim 1, further comprising measuring the second periodic structure.

6. The method of claim 5, wherein said second periodic structure includes a first and a second portion, wherein the first portion is in the region where the first periodic structure is present and the second portion is in a second region where the first periodic structure is not present, and the second periodic structure is measured by measuring said second portion of said second periodic structure in the second region.

7. The method of claim 5, wherein the second periodic structure is measured by illuminating the second periodic structure with incident radiation and by detecting diffracted radiation from the illuminated portions of the second periodic structure.

8. The method of claim 1, wherein measuring the relative position between the first and second periodic structures determines a misalignment between a first and a second layer that were formed respectively together with the first and second periodic structures.

9. The method of claim 1, wherein a first portion of said second periodic structure is in a first region where the first periodic structure is present, and the measuring of the relative position between the first and second periodic structures is made by illuminating the first and second periodic structures in the first region with incident radiation and by detecting diffracted radiation from the first and second periodic structures in said first region.

10. The method of claim 9, wherein a second portion of said second periodic structure different from the first portion is in a second region where the first periodic structure is not present.

11. A method for measuring a relative position between a first and a second layer of a device, a first periodic structure having been formed with the first layer of the device and a second periodic structure having been formed with the second layer of the device, said second periodic structure overlying or interlaced with said first periodic structure, said method comprising:
    measuring a width of at least one of the first and second periodic structures in a first region where the at least one periodic structure is present and the other periodic structure is not present, said measuring including detecting a diffraction of electromagnetic radiation from the periodic structure that is measured, wherein measurement of at least one of the first and second periodic structures is performed without measuring the other one of the first and second periodic structures; and
    measuring a relative position between the first and second layers in a second region different from the first region, where the first and second periodic structures are present in said second region, wherein said measuring of the relative position includes determining a misalignment between the first and second periodic structures.

12. The method of claim 11, said measuring of the width including detecting the zeroth or the first order diffraction from the first and second periodic structures.

13. The method of claim 11, wherein said determining determines the misalignment between the first and second periodic structures from a diffraction from the first and second periodic structures.

* * * * *